(12) United States Patent
Minty et al.

(10) Patent No.: US 11,859,230 B2
(45) Date of Patent: Jan. 2, 2024

(54) COMPOSITIONS AND METHODS FOR MICROBIAL CO-CULTURE

(71) Applicant: The Regents of the University of Michigan, Ann Arbor, MI (US)

(72) Inventors: Jeremy Minty, Ann Arbor, MI (US); Marc E. Singer, Ann Arbor, MI (US); Xiaoxia Lin, Ann Arbor, MI (US); David Boyer, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 132 days.

(21) Appl. No.: 16/304,336

(22) PCT Filed: May 26, 2017

(86) PCT No.: PCT/US2017/034696
§ 371 (c)(1),
(2) Date: Nov. 26, 2018

(87) PCT Pub. No.: WO2017/205750
PCT Pub. Date: Nov. 30, 2017

(65) Prior Publication Data
US 2019/0136271 A1 May 9, 2019

Related U.S. Application Data

(60) Provisional application No. 62/341,984, filed on May 26, 2016.

(51) Int. Cl.
| | | |
|---|---|---|
| C12P 7/48 | (2006.01) | |
| C12M 1/00 | (2006.01) | |
| C12P 39/00 | (2006.01) | |
| C12P 13/02 | (2006.01) | |

(52) U.S. Cl.
CPC ............ *C12P 7/48* (2013.01); *C12M 23/58* (2013.01); *C12P 13/02* (2013.01); *C12P 39/00* (2013.01)

(58) Field of Classification Search
CPC . C12P 7/48; C12P 13/02; C12P 39/00; C12M 23/58
See application file for complete search history.

(56) References Cited

U.S. PATENT DOCUMENTS

| | | | | | |
|---|---|---|---|---|---|
| 3,068,154 | A | * | 12/1962 | Majors | C12M 23/34 |
| | | | | | 435/840 |
| 5,439,817 | A | * | 8/1995 | Shetty | C11D 3/0078 |
| | | | | | 435/221 |
| 6,403,825 | B1 | * | 6/2002 | Frappier | C07C 67/08 |
| | | | | | 560/176 |
| 2003/0124674 | A1 | | 7/2003 | Lee et al. | |
| 2006/0257923 | A1 | * | 11/2006 | Emalfarb | C12N 9/1077 |
| | | | | | 435/6.16 |
| 2008/0044501 | A1 | | 2/2008 | Lee et al. | |
| 2009/0305364 | A1 | * | 12/2009 | Burgard | C12P 13/005 |
| | | | | | 435/243 |
| 2010/0015696 | A1 | | 1/2010 | Claes et al. | |
| 2013/0065282 | A1 | * | 3/2013 | Tran | C12P 7/6463 |
| | | | | | 435/134 |
| 2015/0203880 | A1 | * | 7/2015 | Stephanopoulos | C12P 15/00 |
| | | | | | 435/254.2 |
| 2016/0090614 | A1 | * | 3/2016 | Medoff | G21K 5/00 |
| | | | | | 435/99 |
| 2018/0080055 | A1 | * | 3/2018 | Mao | C12N 9/1048 |

FOREIGN PATENT DOCUMENTS

| | | | |
|---|---|---|---|
| CN | 1036406 A | * | 10/1989 |
| CN | 1556859 A | | 12/2004 |
| CN | 100999756 B | | 7/2007 |
| CN | 101538603 A | | 9/2009 |
| CN | 101838619 A | | 9/2010 |
| CN | 102586353 A | | 7/2012 |
| CN | 105385717 A | | 3/2016 |
| EP | 0611823 B1 | | 11/1999 |
| WO | WO-2013023938 A1 * | 2/2013 | ............ C12P 21/00 |
| WO | WO 2017205750 | | 11/2017 |

OTHER PUBLICATIONS

Lei et al. int. J. Food Prop. (2015) 18(3): 547-557 (Year: 2015).*
Lu et al. Int. J. Appl. Sci. Engineer. (2004) 2(1): 49-58 (Year: 2004).*
Richard et al. Biochem. Engineer. J. (2006) 30: 303-307 (Year: 2006).*
Machine translation of Shi et al. (CN 100999756 A to Shi et al. published 2007) downloaded from the EPO on Sep. 8, 2020 (Year: 2007).*
Machine translation of CN-1036406-A published 1989 downloaded from the EPO on Sep. 10, 2020 (Year: 1989).*
Nugroho et al. Jurnal Teknologi Linkungan (2015) 7(1): 17-23 (Year: 2015).*
English translation of Nugroho J. Environmental Technology (Jurnal Teknologi Linkungan) (2015) 7(1): 17-23 (Year: 2015).*
Kunioka et al. Biosynthesis of poly( gamma-glutamic acid) from L-glutamic acid, citric acid, and ammonium sulfate in Bacillus subtilis IFO3335. Appl Microbiol Biotechnol (1994), 40, 867-872. (Year: 1994).*
Jernejc et al. Citric Acid Production in Chemically Defined Media by Aspergillus niger. European J Appl Microbiol Biotechnol (1982), 14, 29-33. (Year: 1982).*
Bajaj et al., "Poly (glutamic acid)—an emerging biopolymer of commercial interest." Bioresour Technol. May 2011;102(10):5551-61.
Bourdichon, F., et al., "Food fermentations: microorganisms with technological beneficial use.", Int J Food Microbiol. Mar. 15, 2012;154(3):87-97.
Do, J.H. et al., "Efficient recovery of gamma-poly (glutamic acid) from highly viscous culture broth.", Biotechnol Bioeng. Nov. 2001;76(3):219-23.

(Continued)

*Primary Examiner* — Sean C. Barron
(74) *Attorney, Agent, or Firm* — Casimir Jones, S.C.; Tanya A. Arenson

(57) ABSTRACT

Provided herein are compositions and method for producing γ-polyglutamic acid (PGA). In particular, provided herein are bacterial co-culture systems and methods for producing PGA.

12 Claims, 12 Drawing Sheets

(56) References Cited

OTHER PUBLICATIONS

Minty, J.J., et al., "Design and characterization of synthetic fungal-bacterial consortia for direct production of isobutanol from cellulosic biomass.", Proc Natl Acad Sci U S A. Sep. 3, 2013;110(36):14592-7.
Roehr, M. et al., "Citric Acid", in Biotechnology Set. Wiley-VCH Verlag GmbH .2008, p. 307-345.
Rymowicz, W., et al., "Citric acid production from raw glycerol by acetate mutants of Yarrowia lipolytica", 2006. Oct. 2006, vol. 60, Issue 5, pp. 391-394.
Shih et al., "Microbial production of a poly($\gamma$-glutamic acid) derivative by Bacillus subtilis." Process Biochemistry, vol. 40, Issue 8, Jul. 2005, pp. 2827-2832.
Vaughn et al., "Evaluation of alternatives to guar gum as tackifiers for hydromulch and as clumping agents for biodegradable cat litter" Industrial Crops and Products, 2013. 43: p. 798-801.
International Search Report of related PCT/US2017/034696, dated Aug. 23, 2017, 11 pages.
Berovic, M et al. Citric acid production. Biotechnol Annu Rev. 2007; 13, p. 13011-18.
Ogunleye, A et al. Poly-y-glutamic acid: production, properties and applications. Microbiology. 2015. 161(1); p. 1-17.
Shi, F., et al. Microbial production of natural poly amino acid. Science in China Series B: Chemistry. 2007; 50(3), p. 291-303.
Yu, X. et al. Progress in biosynthesis and application of $\gamma$-polyglutamic acid. Journal of Fermentation Technology. 2012; 41(3), p. 12-16. Abstract.

\* cited by examiner

COMPOSITIONS AND METHODS FOR MICROBIAL CO-CULTURE

CROSS-REFERENCE TO RELATED APPLICATIONS

This application claims priority to provisional patent application No. 62/341,984, filed May 26, 2016, which is herein incorporated by reference in its entirety.

STATEMENT REGARDING FEDERALLY SPONSORED RESEARCH OR DEVELOPMENT

This invention was made with government support under Grant Nos. 1355957 and 1448990 awarded by the National Science Foundation. The government has certain rights in the invention.

FIELD OF DISCLOSURE

Provided herein are compositions and method for producing γ-polyglutamic acid (PGA). In particular, provided herein are microbial co-culture systems and methods for producing PGA.

BACKGROUND OF THE DISCLOSURE

γ-polyglutamic acid (PGA) is an anionic polymer of glutamic acid that has a wide range of potential commercial applications due to its unique properties of being absorbent, non-toxic, biodegradable, non-immunogenic, and rich in available carboxylate groups (Bajaj and Singhal, 2011). PGA is a relatively new material, but commercial interest in it is growing.

PGA can be produced through chemical polymerization of glutamic acid, or via microbial biosynthesis, with the latter being more cost-effective. However, microbial biosynthesis requires the addition of citric acid and other reagents, which increases costs.

Improved methods for producing PGA are needed.

SUMMARY OF THE DISCLOSURE

Provided herein are compositions and method for producing γ-polyglutamic acid (PGA). In particular, provided herein are bacterial co-culture systems and methods for producing PGA.

In some embodiments, provided herein is a method of producing γ-polyglutamic acid (PGA), comprising: a) contacting a fungus with a first feedstock; b) fermenting the fungus to generate citric acid; c) contacting the citric acid from step b) with a Bacillus sp. and a second feedstock; and d) fermenting the Bacillus sp. bacteria to generate PGA. In some embodiments, the one or more steps further comprise the addition of one or more of glycerol, glutamate, or glutamine. In some embodiments, steps b) and d) are conducted in the same or different bioreactors. The present disclosure is not limited to a particular fungus. Examples include, but are not limited to, Aspergillus niger, Yarrowia lipolytica, or Candida oleophila. The present disclosure is not limited to particular bacteria. Examples include, but are not limited to, Bacillus subtilis (e.g., strains IFO 3335, TAM-4, C1, C10, chungkookjang, NX-2, MR-141, CGMCC 0833, R23, ER1001, ER1007, ER1064, ER1012, or RKY3) or Bacillus licheniformis (e.g., strains SAB-26, A35, ATCC 9945, CC 12826, WBL-3, or NCIM 2324). In some embodiments, the citric acid is isolated following step b). In some embodiments, the first and second feedstocks are selected from, for example, molasses, raffinate, pomace, fruit peels, corn starch, wheat starch, sorghum, brewery wastes, corn stover, spent algae cake, or glycerol. In some embodiments, the first and second feedstocks are by-products from crop and food processing, biofuel or biochemical production, or biodiesel production. In some embodiments, the bioreactor comprises one or more components selected from, for example, a sparger, a mixing/agitation system, a temperature control system, a pH control system, or an antifoam control system. In some embodiments, the mixing/agitation system is, for example, one or more of impellers, turbines, or paddles driven by a motor. In some embodiments, the step a) or b) further comprises contacting the fungus bacteria with one or more additional components selected from, for example a nitrogen source, a phosphorus source, a carbon source, a salt, or one or more additional nutrients. In some embodiments, the nitrogen source is present at a concentration of approximately 0.1-50 g total N/L and is selected from, for example, yeast extract, peptone, tryptone, urea, corn steep liquor, malt extract, soy bean meal, soytone, $(NH_4)_2SO_4$, $NH_4Cl$, $NH_4NO_3$, $KNO_3$, or $NaNO_3$. In some embodiments, the phosphorus source is present at a concentration of approximately 0.1-25 g total P/L and is selected from, for example, $KH_2PO_4$, $K_2HPO_4$, or $Na_2HPO_4$. In some embodiments, the first and second feedstocks are present at a concentration of 2.5-75% v/v or 50-250 g/L. In some embodiments, the salts are selected from, for example, $KH_2PO_4$, $K_2HPO_4$, $Na_2HPO_4$, $MgSO_4$, $FeCl_3$, $FeCl_2$, $CaCl_2$, $MnSO_4$, NaCl, KCl, and $Na_2SO_4$. In some embodiments, the one or more nutrients are biotin and/or vitamins. In some embodiments, steps a) and b) are performed at an aeration rate of approximately 0.1 to 2 vvm, a pH of approximately 2-8, a temperature of approximately 25-50° C., and an agitation rate of approximately 50-1000 ppm.

Additional embodiments provide a system, comprising: a) a first bioreactor comprising a fungus and a first feedstock; b) a second bioreactor comprising citric acid fermented in the first bioreactor, a Bacillus sp. and a second feedstock.

Further embodiments provide a system, comprising: a bioreactor comprising a fungus, a first feedstock, citric acid fermented from the fungus, a Bacillus sp. and a second feedstock.

Additional embodiments are described herein.

DESCRIPTION OF THE FIGURES

FIG. 1 shows an exemplary compartmentalized sequential bioreactor cultures for producing PGA with glutamic acid independent Bacillus sp.

DEFINITIONS

Figure 1:
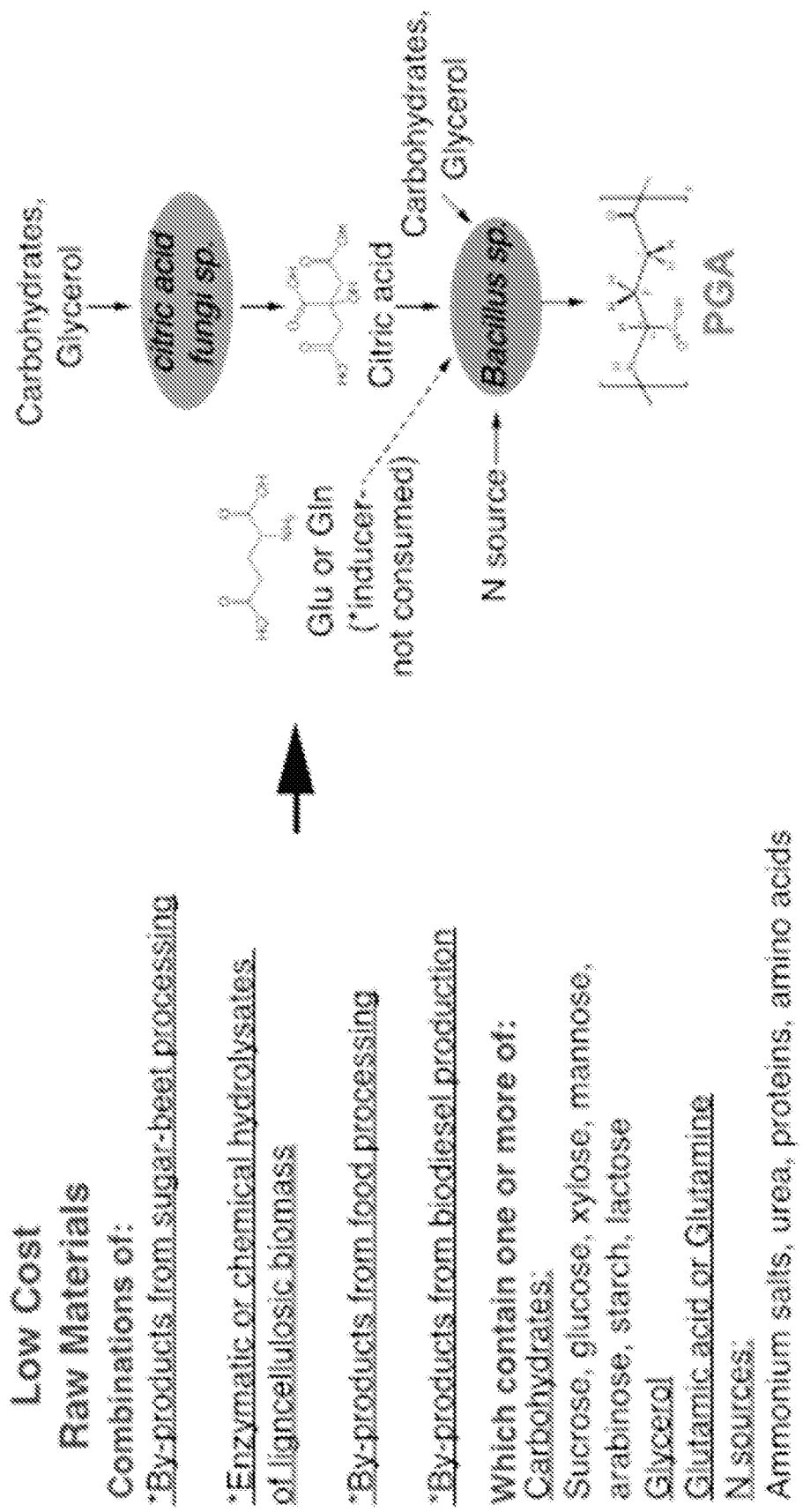
FIG. 1 shows exemplary co-culture for manufacturing PGA via in-situ precursor production (ISPP).

To facilitate an understanding of the present invention, a number of terms and phrases are defined below:

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

As used herein, the term "prokaryotes" refers to a group of organisms that usually lack a cell nucleus or any other membrane-bound organelles. In some embodiments, prokaryotes are bacteria. The term "prokaryote" includes both archaea and eubacteria.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "toxic" refers to any detrimental or harmful effects on a subject, a cell, or a tissue as compared to the same cell or tissue prior to the administration of the toxicant.

As used herein, the term "microbe" refers to a microorganism and is intended to encompass both an individual organism, or a preparation comprising any number of the organisms.

As used herein, the term "microorganism" refers to any species or type of microorganism, including but not limited to, bacteria, archaea, fungi, protozoans, mycoplasma, and parasitic organisms.

As used herein, the term "fungi" is used in reference to eukaryotic organisms such as the molds and yeasts, including dimorphic fungi.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces, and Rickettsia*. All forms of bacteria are included within this definition including cocci, bacilli, spirochetes, spheroplasts, protoplasts, etc. Also included within this term are prokaryotic organisms that are Gram-negative or Gram-positive. "Gram-negative" and "Gram-positive" refer to staining patterns with the Gram-staining process, which is well known in the art. (See e.g., Finegold and Martin, Diagnostic Microbiology, 6th Ed., CV Mosby St. Louis, pp. 13-15 (1982)). "Gram-positive bacteria" are bacteria that retain the primary dye used in the Gram-stain, causing the stained cells to generally appear dark blue to purple under the microscope. "Gram-negative bacteria" do not retain the primary dye used in the Gram-stain, but are stained by the counterstain. Thus, Gram-negative bacteria generally appear red.

As used herein, the term "cell culture" refers to any in vitro culture of cells, including, e.g., prokaryotic cells and eukaryotic cells. Included within this term are continuous cell lines (e.g., with an immortal phenotype), primary cell cultures, transformed cell lines, finite cell lines (e.g., non-transformed cells), bacterial cultures in or on solid or liquid media, and any other cell population maintained in vitro.

DETAILED DESCRIPTION OF THE DISCLOSURE

Provided herein are compositions and method for producing γ-polyglutamic acid (PGA). In particular, provided herein are bacterial co-culture systems and methods for producing PGA.

PGA has multiple commercial uses (See e.g., Table 1 below). PGA is produced naturally by many *Bacillus* sp.

bacteria, and occurs most abundantly in natto, a traditional Japanese food produced by fermenting soybeans with *Bacillus subtilis* "natto" strains. PGA producing *Bacillus* sp. are metabolically versatile and are capable of utilizing a wide range of carbon sources to synthesize PGA and polysaccharide co-products such as levan (Bajaj and Singhal, Bioresource Technology, 5551-5561, 2011). The most widely utilized strains are *B. licheniformis* ATCC 9945 and 9945A, and *B. subtilis* "natto" strains, of which *B. subtilis* natto IFO3335 is well known. For *B. licheniformis* ATCC 9945, PGA production is optimal when citric acid, glutamic acid, and glycerol are provided as carbon sources (Bajaj and Singhal, 2011; supra). *B. subtilis* IFO3335 produces PGA with high yield and selectivity using citric acid as the carbon source and glutamic acid or glutamine as an inducer. Under these conditions, PGA is synthesized with high selectivity (minimal polysaccharide side product) from endogenously produced glutamic acid (glutamine and glutamic acid present in the media act as inducers, but are not consumed), with titers up to 20 g/L and yields of 0.6 mol PGA/mol citric acid (Bajaj and Singhal, 2011). However, these methods require addition of citric acid during production, thus increasing production costs. Accordingly, provided herein are improved co-culture methods that do not require the addition of purified citric acid.

For example, in some embodiments, provided herein are microbial co-cultures for efficient PGA production via in-situ precursor production, using low cost raw materials (See e.g., FIG. 1). The systems and methods described herein provide co-culture systems and methods that utilize a first fermentation reaction to generate citric acid and a second fermentation reaction that generates PGA. The present disclosure is not limited to specific reagents and microorganisms for fermentation. Exemplary, non-limiting microorganisms and reagents are described below and in FIG. 1.

In the scheme shown in FIG. 1, low-cost raw materials are fermented to citric acid by fungi (e.g., *Aspergillus niger* or *Yarrowia lipolytica* or other suitable fungus) (stage 1). In the next step (stage 2), citric acid produced in stage 1 (and depending on species, glycerol) are converted to PGA by glutamic-acid independent PGA-producing *Bacillus* sp, wherein PGA production is induced by glutamate or glutamine, or is completely independent of glutamate or glutamine, but these substances are not actually consumed by *Bacillus* sp.

The present disclosure provides the advantage of producing citric acid in-situ via fermentation of lower-cost materials (e.g., sugars). Compared to having to purchase citric acid pre-cursor, in-situ production reduces raw materials costs. In some embodiments, fermentation is integrated into a full bioprocess for producing PGA (raw material preparation/pre-treatment, ISPP fermentation, purification, and final drying/milling/packing), and substantially reduce the overall cost of production of PGA.

TABLE 1

| Market | Application | Biochemical Functionality |
|---|---|---|
| Food | Thickener/Stabilizer | Viscosity |
| | Texture Enhancer | Texture improvement for bread/noodles |
| | Animal Feed Supplement | Chelation - enhanced mineral absorption for improved bone growth, egg shell strength, etc. |
| Healthcare | Nutrition Supplement | Chelation - enhanced $Ca^{2+}$ absorption, possibly beneficial for osteoporosis |
| | Drug carrier/tissue scaffold | Biocompatible, non-immunogenic and suitable for conjugation to a variety of drugs/substrates |
| | Medical adhesive | |
| Cosmetics | Moisturizer | Humectant, reduction of trans-epidermal water loss, enhancement of epidermis integrity, inhibition of hyaluronidase, potentially reduces appearance of wrinkles and fine lines via moisturization/plumping |
| Personal Care | Superabsorbent material (diapers, etc) | Water absorbency |
| Water treatment | Flocculant | Precipitation/removal of particulates |
| | Heavy metal removal | Chelation of various heavy metals and radioisotopes |
| Agriculture | Soli conditioner | Improvement of soil texture and erosion reduction via adhesion effects; improved water retention; slow-release nitrogen source |

I. Fermentation Reagents

As described herein, the present disclosure provides co-culture systems and methods for producing PGA. Exemplary microorganisms and reagents are described below.

A. Feedstocks

In some embodiments, fermentation reactions (e.g., PGA fermentation and/or citric acid fermentation) utilize carbohydrate feedstocks as a feed source for fermentation microorganisms. The present disclosure is not limited to a particular feedstock for use in producing PGA. Primary feedstocks are chosen on the basis of cost, required supply scale, composition of nutrients (such as carbon sources, nitrogen sources, and salts) conducive to citric acid and/or PGA production, level of contaminants or impurities that inhibit microbial growth or metabolite production, and satisfaction of any applicable regulations or certifications for the final PGA product (e.g., USDA Organic). Examples of nutrients that are useful for citric acid and/or PGA production are given in FIG. 1 and Table 2. Examples of low-cost primary feedstock materials, containing useful nutrients and being desirable for PGA production using the co-culture schemes, are depicted in FIG. 1 and given in Table 3. It should be understood that various combinations of primary feedstocks, as well as supplemental nutrients, can be used, and that these lists are not exhaustive.

In some embodiments, additional nutrients and/or micronutrients are utilized in stage 1 or 2 fermentation reactions. Exemplary nutrients and/or micronutrients and suitable concentrations are shown in Tables 7-8.

TABLE 2

Examples of useful nutrients for production
of PGA via ISPP co-culture schemes

| Nutrient type | Examples |
|---|---|
| Carbon sources | Carbohydrates: sucrose, glucose, xylose, arabinose, mannose, lactose, maltose, starch, sorbitol, manitol<br>Glycerol |
| PGA inducers/precursors | Amino acids: glutamic acid, glutamine<br>TCA cycle intermediates: pyruvic acid, citric acid, α-ketoglutaric acid |
| Nitrogen sources | Organic: Yeast extract, peptone, tryptone, urea, corn steep liquor, malt extract, soy bean meal, soytone<br>Inorganic: $(NH_4)_2SO_4$, $NH_4Cl$, $NH_4NO_3$, $KNO_3$, $NaNO_3$ |
| Salts | $KH_2PO_4$, $K_2HPO_4$, $Na_2HPO_4$, $MgSO_4$, $FeCl_3$, $FeCl_2$, $CaCl_2$, $MnSO_4$, $NaCl$, $KCl$, $Na_2SO_4$ |
| Other nutrients/supplements | Biotin, vitamins |

TABLE 3

Examples of desirable low-cost primary feedstocks (containing one or
more of useful nutrients) for PGA production via ISPP co-cultures

| Class | Examples |
|---|---|
| Crop and food processing residues | Sugar cane processing by-products (molasses, raffinate)<br>Sugar beet processing by-products (molasses, raffinate)<br>By-products from other fruit and vegetable processing (such as waste pomace or peels)<br>Starch from grains such as corn, wheat, or sorghum<br>Brewery wastes<br>Enzymatic or chemical hydrolysates of lignocellulosic biomass, such as corn stover or switchgrass |
| Residues from biofuel or biochemical production | Stillage from ethanol production from non-cellulosic carbohydrates, such as sugar beets or sugar cane<br>Stillage from cellulosic ethanol production, such as corn stover ethanol<br>Stillage from production of bulk biochemicals, such as glutamic acid or lysine fermentation residues<br>Residues, such as spent algae cake, from production of algal biofuels |
| Residues from biodiesel production | Waste glycerol from chemical or enzymatic transesterification of vegetable or algae oils |

B. Citric Acid Fermentation

Stage 1 of the PGA production process comprises fungal production of citric acid. The present disclosure is not limited to particular fungi for use in producing citric acid. The specific citric acid producing fungi are selected on the basis of one of more properties such as, including but not limited to, ability to efficiently utilize desired raw materials, produce citric acid at high titer (final concentration), yield (mass citric acid per mass raw material consumed), and productivity (rate of production), high tolerance to inhibitory or toxic molecules found in the raw materials (e.g., salts, organic acids, etc), minimal nutrient requirements, low or no production of anti-bacterial compounds, and maximum environmental compatibility with PGA producing *Bacillus* sp., including compatible growth temperatures, pH, salinity/osmolarity, and dissolved oxygen levels, insensitivity to Mn or other divalent metals, and insensitivity to nitrogen concentration. With the understanding that this list is not exhaustive, examples of suitable citric acid producing fungi species and strains are given in Table 4.

The bioreactor is charged with an aqueous mixture of primary feedstocks and additional nutrients (nitrogen and phosphorus source) suitable for fungal citric acid fermentation, such as those given in Table 6, which have been pre-treated as appropriate (e.g., beet molasses may be precipitated with ferrocyanide to remove trace metals). Primary feedstocks, nitrogen sources, and phosphorus sources including but not limited to those listed in Table 6 are used singly or in various combinations, and formulated as per the appropriate concentration ranges, such as those listed in Table 6. In some embodiments, the final growth media (comprising the aqueous mixture of primary feedstocks and additional nutrients) has total C source concentration, C:N, C:P, trace metal concentration, and Mn concentration that are conducive to citric acid fermentation, including but not limited to the ranges listed in Table 8. In some embodiments, the aqueous mixture of feedstock and nutrients is pasteurized or sterilized with heat (e.g., heated to 121° C. for 25-30 minutes with steam) or filtration (e.g., filtered through 0.22 μm membrane) to eliminate microbial contamination, which can be done before or after adding to the bioreactor.

The bioreactor is then inoculated with a smaller (e.g., 1/10 to 1/10,000 volume) culture of citric acid producing fungi, including but not limited to one or more of the strains listed in Table 4, which are prepared using standard fungal microbiology. In some embodiments, *Aspergillus* sp. (e.g., strains listed in Table 4) are use when the primary feedstock is rich is carbohydrates (such as the crop and food processing residues listed in Table 6), while *Yarrowia* or *Candida* sp. (e.g., strains listed Table 4) are used for glycerol rich primary feedstocks (e.g., such as waste glycerol from biodiesel production). After inoculation, the bioreactor aeration rate, agitation rate, pH, and temperature are maintained so as to promote fungal fermentation of carbohydrate or glycerol fractions of the primary feedstock into citric acid. Examples of aeration, agitation, pH, and temperature parameters suitable for fungal citric acid fermentation are given in Table 8, with the understanding that useful parameters and ranges are not limited to those given here. The citric acid fermentation is conducted for sufficient duration to maximize the final titer (concentration) and yield (g citric acid per g primary feedstock), with typical fermentation times given in Table 8. During the course of citric acid fermentation, the fungi consume primary feedstock and additional nutrients, and secrete citric acid, producing a citric acid rich culture broth.

After the citric acid fermentation is completed, the citric acid rich culture broth is transferred to a second bioreactor to serve as a primary feedstock for PGA fermentation. The second bioreactor is charged with raw citric acid rich culture broth, or alternately the residual fungal biomass in the citric acid rich culture broth is removed by standard methods (e.g., centrifugation or filtration through 0.22 μm membrane), and/or deactivated by pasteurization or sterilization with heat (e.g., heated to 121° C. for 25-30 minutes with steam).

TABLE 4

Examples of citric acid producing fungi for ISPP co-cultures.

| Species | Strains |
|---|---|
| *Aspergillus niger* | ATCC 9142 |
|  | GCM 7 |
|  | TT 55 |
|  | GCMC-7 |
|  | IM-155 |
|  | YANG No. 2 |
|  | YW-112 |
|  | NRRL 2001 |
|  | NRRL 2270 |
|  | NRRL 328 |
|  | NRRL 567 |

TABLE 4-continued

Examples of citric acid producing fungi for ISPP co-cultures.

| Species | Strains |
|---|---|
| | NRRL 599 |
| | BC1 |
| | LPB-21 |
| | CFTRI-30 |
| | ATCC 1015 |
| | ACM 4942 |
| Yarrowia lipolytica | NRRL Y-1095 |
| | NRRL Y-1094 |
| | NRRL Y-7576 |
| | ATCC 8661 |
| | ATCC 20320 |
| | ATCC 20324 |
| | ATCC 20346 |
| | ATCC 20390 |
| | ATCC 20114 |
| Candida oleophila | ATCC 20177 |

TABLE 5

Primary feedstocks and nutrients for fungal citric acid fermentation, with desirable formulation ranges.

| Category | Component | Concentration |
|---|---|---|
| Primary Feedstocks | Sugar cane molasses | 10-75% v/v |
| | Sugar beet molasses | 10-75% v/v |
| | Lignocellulosic biomass hydrolysate | 10-100% v/v |
| | Starch | 50-500 g/L |
| | Brewery wastes | 50-500 g/L |
| | Fruit/vegetable processing wastes | 50-500 g/L |
| | Waste glycerol (biodiesel by-product) | 2.5-95% v/v |
| Additional Nutrients | Nitrogen sources (Yeast extract, peptone, tryptone, urea, corn steep liquor, malt extract, soy bean meal, soytone, $(NH_4)_2SO_4$, $NH_4Cl$, $NH_4NO_3$, $KNO_3$, and/or $NaNO_3$) | 0.1-5 g total N/L |
| | Phosphorus sources ($KH_2PO_4$, $K_2HPO_4$, and/or $Na_2HPO_4$) | 0.1-5 g total P/L |

C. PGA Production

Stage 2 of the fermentation process comprises PGA production by a PGA producing Bacillus strain. The present disclosure is not limited to a particular PGA producing strain. In some embodiments, the specific γ-polyglutamic acid (PGA) producing Bacillus sp. are selected on the general basis of one or more properties including, but not limited to, preferential ability to efficiently utilize citric acid produced from desired raw materials in the first step, produce PGA at high titer (final concentration), yield (mass PGA per mass raw material consumed), and productivity (rate of production), high tolerance to inhibitory or toxic molecules found in the raw materials (e.g., salts, organic acids, etc.), minimal nutrient requirements, and maximum environmental compatibility with citric acid producing fungi, including compatible growth temperatures, pH, salinity/osmolarity, and dissolved oxygen levels, and ability to utilize nitrogen sources that do not interfere with citric acid production. With the understanding that this list is not exhaustive, examples of suitable PGA producing Bacillus species and strains are given in Table 5.

In some embodiments, Bacillus sp. that decouple PGA production from exogenous glutamic acid or glutamine are utilized. Such strains may be completely independent of exogenous glutamic acid or glutamine (e.g., produce PGA whether or not exogenous glutamic acid or glutamine is present), or may function such that exogenous glutamic acid or glutamine act as inducers for PGA biosynthesis, but are not actually consumed. With the understanding that this list is not exhaustive, examples of preferred strains of PGA producing Bacillus species that decouple PGA production from exogenous glutamic acid or glutamine are given in the top half of Table 5.

The PGA fermentation step can be performed using any suitable Bacillus sp. culturing method and apparatus (e.g., test tubes, flasks, petri dishes, or bioreactor). In some embodiments, fermentation is conducted in a bioreactor equipped with a sparger (to provide aeration via compressed air), mixing/agitation system (e.g., impellers, turbines, or paddles linked to a motor), temperature control system, pH control system, and antifoam control system.

The bioreactor is charged with an aqueous mixture of citric acid rich fungal culture broth (e.g., as described above), which serves as the primary feedstock, additional secondary feedstocks, and additional nutrients (PGA precursors/inducers, nitrogen sources, salts, phosphorus sources, and other supplements) suitable for PGA fermentation, such as those given in Table 7, which have been pre-treated as appropriate (e.g., as per the possible fungal biomass removal and/or pasteurization or sterilization described above for fungal citric acid culture broth). Primary feedstock, secondary feedstocks, PGA precursors or inducers, nitrogen sources, phosphorus sources, metal salts, trace elements, and other supplements, including but not limited to those listed in Table 7, are used singly or in various combinations, and formulated as per the appropriate concentration ranges, such as those listed in Table 7. In some embodiments, the final growth media (e.g., comprising the aqueous mixture of primary feedstock and additional nutrients) has total C source concentration, C:N, C:P, metal salts/trace metal concentrations, PGA inducer/precursor concentrations, and Mn concentrations that are conducive to PGA fermentation, including but not limited to the ranges listed in Table 8. The usage of PGA inducer/precursors may or may not be required, depending on the specific PGA biosynthesis characteristics of the PGA-producing Bacillus sp. chosen.

In some embodiments, the aqueous mixture of feedstocks and nutrients is pasteurized or sterilized with heat (e.g., heated to 121° C. for 25-30 minutes with steam) or filtration (e.g., filtered through 0.22 μm membrane) to eliminate microbial contamination, which can be done before or after adding to the bioreactor. The bioreactor is then inoculated with a smaller (1/10 to 1/10,000 volume) culture of PGA producing Bacillus sp., including but not limited to one or more of the strains listed in Table 6, which can be prepared using standard Bacillus sp. microbiology techniques that are well known to those skilled in the art. Bacillus sp. that are capable of fermenting citric acid to PGA in high titer (final concentration) and yield (g-PGA per g citric acid), and that are glutamic-acid independent, wherein PGA production is induced by exogenous glutamic acid or glutamine, or occurs independently of glutamic acid or glutamine, are preferred, including but not limited to such strains listed in Table 6.

After inoculation, the bioreactor aeration rate, agitation rate, pH, and temperature are maintained so as to promote Bacillus sp fermentation of citric acid, accompanying secondary feedstocks, and additional nutrients into PGA. Examples of aeration, agitation, pH, and temperature parameters suitable for this fermentation are given in Table 8, with the understanding that useful parameters and ranges are not limited to those given here. The PGA fermentation is conducted for sufficient duration to maximize the final titer (concentration) and yield (g PGA per g citric acid), with typical fermentation times given in Table 8. During the course of PGA fermentation, the Bacillus sp. ferments citric acid and accompanying secondary feedstocks into PGA, a process which may be accelerated by PGA precursors or inducers, depending on the characteristics of the specific strain used. In some embodiments, after the PGA fermentation is completed, the PGA rich culture broth is harvested from the second bioreactor and further processed and purified to yield the final desired PGA product, using any combination of cell removal and PGA extraction/purification methods (e.g., those described herein).

TABLE 6

*Bacillus* strains

| Characteristic | Species | Strains |
|---|---|---|
| Preferred strains of glutamic-acid independent *Bacillus* sp, wherein PGA production is induced by exogenous glutamic acid or glutamine, or occurs independently of glutamic acid or glutamine | *Bacillus subtilis* | IFO 3335 |
| | *Bacillus subtilis* | TAM-4 |
| | *Bacillus licheniformis* | SAB-26 |
| | *Bacillus licheniformis* | A35 |
| | *Bacillus subtilis* | C1 |
| | *Bacillus subtilis* | C10 |
| Glutamic-acid consuming strains of PGA-producing *Bacillus* sp, wherein exogenous glutamic acid is partially or fully polymerized to form PGA | *Bacillus licheniformis* | ATCC 9945 |
| | *Bacillus subtilis* | Chungkookjang |
| | *Bacillus licheniformis* | CC 12826 |
| | *Bacillus subtilis* | NX-2 |
| | *Bacillus subtilis* (natto) | MR-141 |
| | *Bacillus licheniformis* | WBL-3 |
| | *Bacillus subtilis* | CGMCC 0833 |
| | *Bacillus subtilis* | R23 |
| | *Bacillus licheniformis* | NCIM 2324 |
| | *Bacillus subtilis* | RKY3 |

TABLE 7

Primary feedstock and nutrients for glutamic acid-interdependent *Bacillus* sp. PGA fermentation, with exemplary formulation ranges.

| Category | Component | Concentration |
|---|---|---|
| Primary feedstock | Citric acid-rich fungal culture broth (with or without viable fungi cells) from first fermentation step | 10-90% v/v |
| Secondary feedstocks | Waste glycerol (biodiesel by-product) | 10-95% v/v |
| | Sugar cane molasses | 10-50% v/v |
| | Sugar beet molasses | 10-50% v/v |
| | Lignocellulosic biomass hydrolysate | 10-50% v/v |
| | Starch | 50-250 g/L |
| | Brewery wastes | 50-250 g/L |
| | Fruit/vegetable processing wastes | 50-250 g/L |
| PGA precursors or inducers | Stillage or other by-products from ethanol production from non-cellulosic carbohydrates, such as sugar beets or sugar cane | 50-500 g/L |
| | Stillage or other by-products from cellulosic ethanol production, such as corn stover ethanol | 50-500 g/L |
| | Stillage or other by-products from production of bulk biochemicals, such as glutamic acid or lysine fermentation residues | 50-500 g/L |
| | Residues, such as spent algae cake, from production of algal biofuels | 50-500 g/L |
| | Amino acids (glutamate, glutamine) | 0-50 g/L |
| | α-ketoglutaric acid | 0-50 g/L |
| Additional Nutrients | Nitrogen sources (Yeast extract, peptone, tryptone, urea, corn steep liquor, malt extract, soy bean meal, soytone, $(NH_4)_2SO_4$, $NH_4Cl$, $NH_4NO_3$, $KNO_3$, and/or $NaNO_3$) | 5-50 g total N/L |
| | Phosphorus sources ($KH_2PO_4$, $K_2HPO_4$, and/or $Na_2HPO_4$) | 1-25 g total P/L |
| | Metal Salts & Trace Elements ($MgSO_4$, $FeCl_3$, $FeCl_2$, $CaCl_2$, NaCl, $MnSO_4$) | 0.01-10 g/L |
| | Other supplements (biotin, vitamins) | 250-1000 ppm |

TABLE 8

Examples of exemplary fermentation parameter ranges for citric acid and PGA fermentation.

| | Citric Acid Fermentation (Bioreactor #1) | | PGA Fermentation (Bioreactor #2) |
|---|---|---|---|
| | | Microbial species | |
| Parameters | *Aspergillus* sp. | *Yarrowia* sp. | *Bacillus* sp. |
| Fermentation time | 2-10 days | 2-14 days | 1-5 days |
| Aeration rate | 0.2-2 vvm | 0.2-2 vvm | 0.1-2 vvm |
| pH | 2-4 | 4.5-7.5 | 6-8 |
| Temperature | 25-35° C. | 25-40° C. | 30-50° C. |
| Agitation rate | 50-1000 rpm | 50-1000 rpm | 50-1000 rpm |

TABLE 8-continued

Examples of exemplary fermentation parameter ranges for citric acid and PGA fermentation.

| | Citric Acid Fermentation (Bioreactor #1) | | PGA Fermentation (Bioreactor #2) |
|---|---|---|---|
| | | Microbial species | |
| Parameters | *Aspergillus* sp. | *Yarrowia* sp. | *Bacillus* sp. |
| Media conditions | 100-300 g/L C source<br>100-1000 C:N (g/g)<br>50-4000 C:P (g/g)<br>0-100 ppm total trace metals<br>0-5 ppm Mn | 20-300 g/L C source<br>100-1000 C:N (g/g)<br>50-4000 C:P (g/g)<br>0-100 ppm total trace metals<br>0-5 ppm Mn | 50-300 g/L C source<br>0.1-10 C:N<br>1-100 C:P<br>1-100 g/L Metal salts & trace metals<br>0-500 g/L PGA inducers or precursors<br>0-1 g/L Mn |

II. Co-Culture Methods

The co-culture scheme discussed above can be deployed in various ways to produce PGA. Exemplary methods for deploying the co-culture schemes of embodiments of the present disclosure are described herein.

Figure 2:
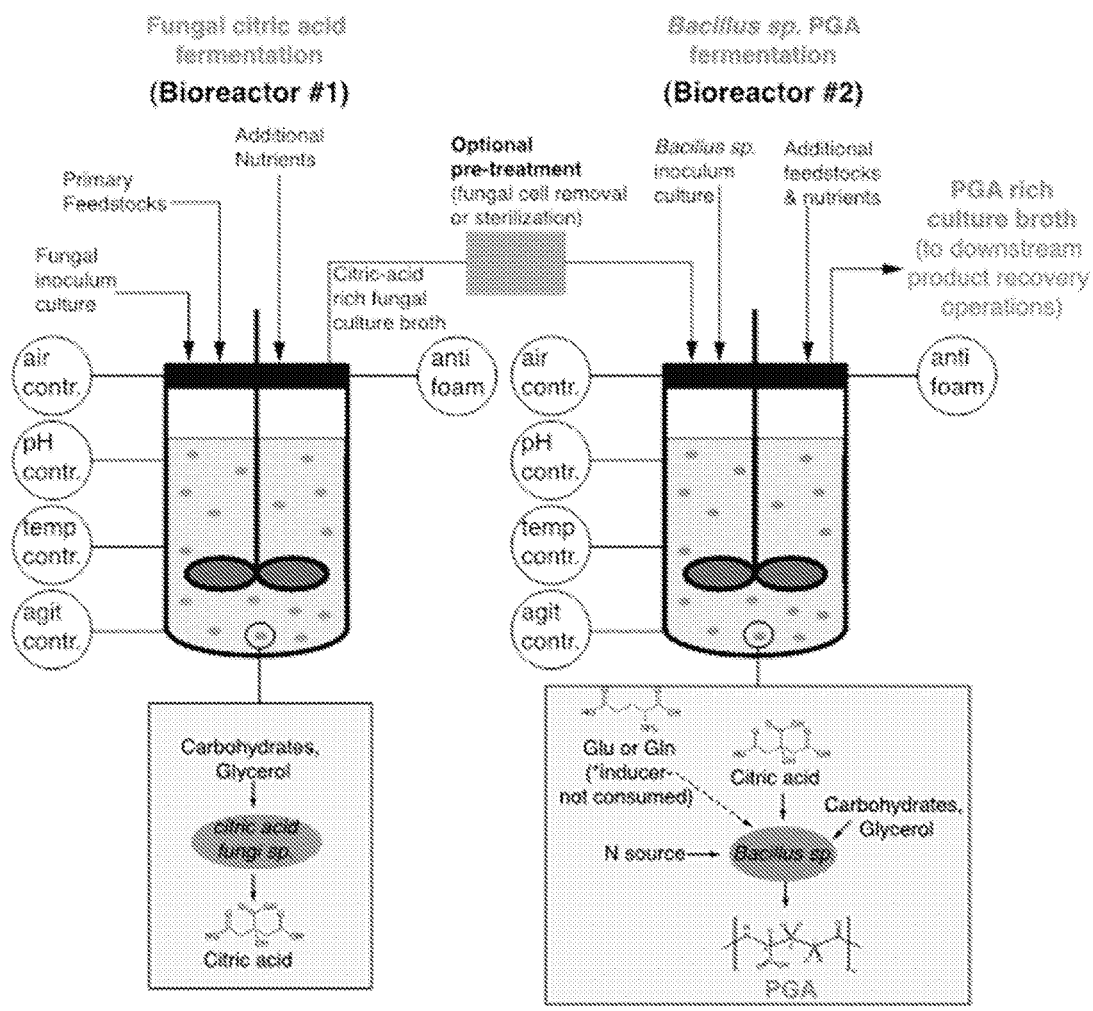
FIG. 2 shows exemplary consolidated sequential cultures for producing PGA with glutamic acid independent Bacillus sp.

In some embodiments, compartmentalized sequential culture methods are utilized (See e.g., FIG. 2). In this method, citric acid producing fungi are first cultured in a bioreactor under permissive conditions, using appropriate feedstocks and nutrients (e.g., as described above). The citric acid rich culture broth is then transferred to a second bioreactor where PGA producing *Bacillus* sp. are cultured under permissive conditions and with appropriate additional feedstocks and nutrient supplements. The *Bacillus* sp. then ferments citric acid and additional feedstocks and nutrients into PGA. PGA containing culture broth from the second bioreactor is then be harvested and purified to yield a final PGA product. In some embodiments, the citric acid rich culture broth from the first bioreactor is treated to remove or deactivate fungal cells before entering the second bioreactor. An overview of the process is shown in FIG. 2.

Figure 3:
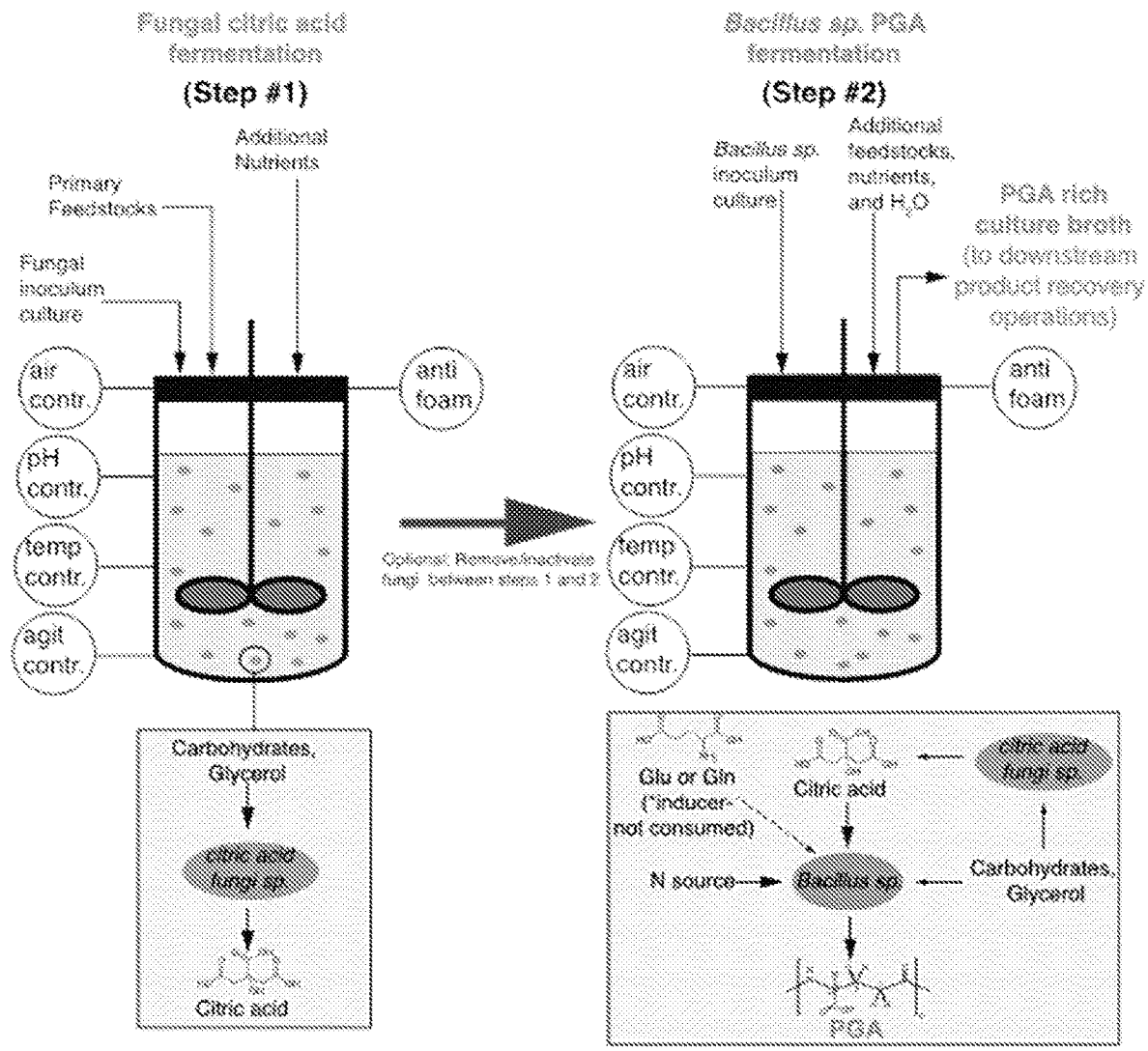
FIG. 3 shows PGA production via compartmentalized sequential cultures of A. niger NRRL 599 and PGA producing Bacillus sp. NRRL 14202. (A) Compartmentalize sequential culture method for solid media. (B) Evidence of PGA production via appearance of mucoid colonies on plates. (C) PGA confirmation by SDS-PAGE.

In some embodiments, stage 1 and stage 2 fermentation are performed in a single bioreactor. In this method, citric acid producing fungi (*A. niger* or *Y. lipolytica*) are cultured in a bioreactor under permissive conditions, using appropriate feedstocks (e.g., sugars or glycerol). After the citric acid fermentation is finished, the bioreactor is directly inoculated with PGA producing *Bacillus* sp. Bioreactor conditions are then shifted to favor PGA producing *Bacillus* sp. and appropriate additional feedstocks and nutrient supplements for PGA producing *Bacillus* sp are added. The *Bacillus* sp. then ferment citric acid and additional feedstocks and nutrients into PGA. PGA containing culture broth from the bioreactor is then be harvested and purified to yield a final PGA product. The fungi may be removed or deactivated before the second step of inoculating the bioreactor with PGA producing *Bacillus* sp. Compared to the compartmentalized sequential cultures (FIG. 2), this method achieves further cost reductions by consolidation into a single bioreactor. An overview of the process is shown in FIG. 3.

In selecting fungal strains for citric acid production with the single bioreactor method, preference is given to fungal strains that have reduced metabolic activity or viability under fermentation conditions favorable for PGA production, are insensitive to nitrogen sources utilized in PGA production, are ecologically compatible with PGA producing *Bacillus* sp. (e.g., that do not produce anti-microbial metabolites under the utilized cultivation conditions, and which otherwise do not interact antagonistically with *Bacillus* sp.), and have minimal capability for citric acid re-uptake under fermentation conditions favorable for PGA production (including but not limited to those strains listed in Table 5).

The citric acid and PGA fermentation steps are performed using any suitable culture method and apparatus known to those skilled in the art (e.g., test tubes, flasks, petri dishes, or bioreactor). In some embodiments, fermentation is conducted in a bioreactor equipped with one or more of a sparger (to provide aeration via compressed air), mixing/agitation system (such as impellers, turbines, or paddles driven by a motor), temperature control system, pH control system, and antifoam control system.

III. Uses

PGA produced using the described methods finds use in a variety of research and commercial uses. In some embodiments, PGA is used in tackifier (Vaughn et al., Industrial Crops and Products, 2013. 43: p. 798-801) or super absorbent polymer production. Cross-linked PGA superabsorbent polymers (SAP) find use in absorbent hygiene product (AHP) applications as other uses. SAPs (typically based on PAC/PAM or starch-graft polymers) are widely used in the absorbent cores of hygiene products, with disposable diapers representing approximately 85% of the global SAP market of $5B (*Trends and Forecast*, 2014-2020. 2015, Transparency Market Research). Increasing consumer preferences for safe and sustainable personal care products have driven the development of eco-friendly and natural labeled AHP brands, particularly diapers, and these products are currently experiencing strong growth (*Trends and Forecast*, 2014-2020. 2015, Transparency Market Research).

EXPERIMENTAL

The following examples are provided in order to demonstrate and further illustrate certain preferred embodiments and aspects of the present invention and are not to be construed as limiting the scope thereof.

Example 1

Figure 4:
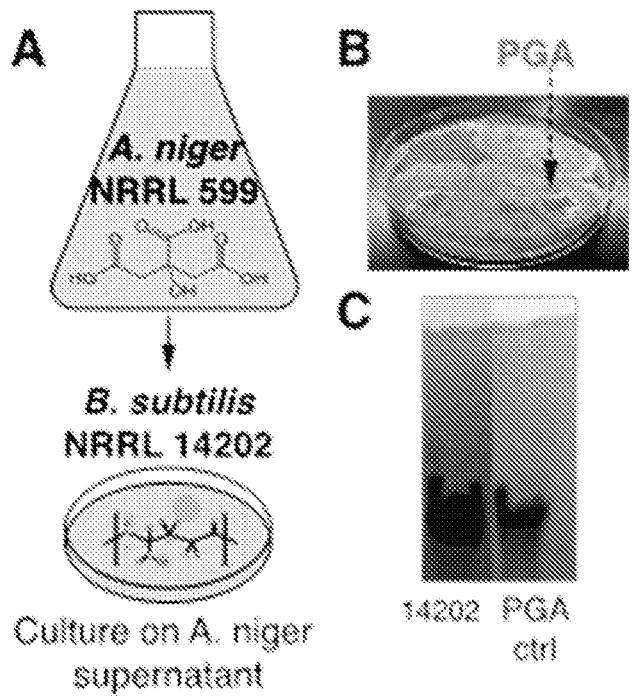
FIG. 4 shows growth of Bacillus subtilis NRRL 14202O ($OD_{600}$ at different time points) in compartmentalized sequential cultures ("A niger (NGPP)" series) and control cultures formulated with commercial citric acid and with similar sucrose concentration to media formulated with A. niger supernatant ("NGPP sucrose ctrl" series).

PGA Production via Compartmentalized Sequential Cultures of *A. niger* NRRL 599 and PGA Producing *Bacillus* sp. NRRL 14202O PGA Producing *Bacillus* sp. NRRL 14202O was cultivated at bench scale on solid and liquid media prepared from supernatant (cell-free culture broth) from citric acid producing *A. niger* cultures grown on sucrose media (see scheme in FIG. 4A illustrating the solid media experiment).

Materials and Methods

Citric acid production with *A. niger* NRRL 599. 5 mL sterile *A. niger* inoculum media (2.50 g/L $(NH_4)_2SO_4$, 0.6 g/L $KH_2PO_4$, 1.66 mM $MgSO_4$, 20 g/L sucrose, 2 g/L yeast extract, and 1 g/L peptone, with pH adjusted to 5.5) was aliquoted to a sterile 50 mL culture tube and inoculated with cryopreserved spores of *A. niger* NRRL 599 (obtained from the USDA ARS culture collection). The inoculated culture was incubated for 48 hours at 30° C. with gentle shaking (150-200 rpm). After 48 hours, the culture was aseptically filtered through a 0.22 µm membrane to removed fungal mycelium. The fungal mycelium was washed repeatedly to remove the inoculum media, and then inoculated into 300 mL of sterile citric acid production media (composed of 2.50 g/L $(NH_4)_2SO_4$, 0.6 g/L $KH_2PO_4$, 1.66 mM $MgSO_4$, and 140 g/L sucrose, pH adjusted to 2.5) in a sterile 1000 mL flask. After inoculation, the flask was sealed with adhesive paper (to provide a porous seal for aeration) and incubated for 9 days at 30° C. with gentle shaking (150-200 rpm). Periodically, 1 mL samples were aseptically taken from the culture for quantification of citric acid and sucrose via HPLC (described below in "Analytical Methods: HPLC analysis of small molecule metabolites"). After 9 days of cultivation, the *A. niger* NRRL 599 culture produced 22.1 g/L citric acid and consumed 80 g/L sucrose (with approximately 60 g/L sucrose remaining).

PGA production with agar plates prepared with *A. niger* NRRL 599 supernatant. After the citric acid fermentation was completed, the pH of the culture broth was adjusted to 7.2 and residual *A. niger* mycelium was removed by aseptic filtration through a 0.22 µm membrane. Non-glycolytic precursor PGA production agar medium (NGPP) was made and sterilized using the *A. niger* supernatant as a citric acid source, with the following composition: 1 g/L $KH_2PO_4$, 1 g/L $K_2HPO_4$, 0.5 g/L $MgSO_4*7H_2O$, 0.05 g/L $FeCl_3*6H_2O$, 0.2 g/L $CaCl_2*2H_2O$, 0.02 g/L $MnSO_4*H_2O$, 7.5 g/L $(NH_4)_2SO_4$, 0.7 g/L yeast extract, 3.5 g/L peptone, 7 g/L glycerol, 11.6 g/L glutamic acid (monohydrate), 0.5 mg/L biotin, 15 g/L agar, and 265.9 mL/L filtered *A. niger* supernatant (yielding 5.9 g/L citric acid in the final media formulation), with the pH adjusted to 7.0. As a control, a separate batch of NGPP media was prepared with commercially available purified citric acid, with 16 g/L sucrose added to control for residual sucrose in the *A. niger* supernatant. The media was poured into 100 mm diameter sterile petri dishes and allowed to solidify. Cryopreserved culture of *Bacillus* sp. NRRL 14202O (obtained from USDA ARS culture collection) was inoculated into 2 mL liquid NGPP media (formulated with commercial citric acid) in a sterile 15 mL culture tube and incubated for 24 hours at 40° C. with gentle shaking (150-200 rpm). After 24 hours of incubation, the cultures were centrifuged and washed, and then aseptically isolation streaked on NGPP plates prepared with fungal supernatant and NGPP plates prepared with commercial citric acid (controls). The plates were wrapped and incubated for 24 hours at 40° C. PGA production was preliminarily assessed by appearance of mucoid colonies. PGA production was confirmed by resuspending mucoid material from each plate in 30 mL 0.85% w/v NaCl, centrifuging to remove cellular matter, and analyzing the resulting supernatant with SDS-PAGE and methylene blue staining (described below in "Analytical methods: PGA quantification via SDS-PAGE").

PGA production on liquid media prepared with *A. niger* NRRL 599 supernatant. NGPP medium was prepared as described above, except that agar was omitted to produce a liquid medium. As above, fungal citric acid supernatant was added at 265.9 mL/L to one batch of media (yielding 5.9 g/L citric acid in the final media formulation), while a control batch was formulated with commercial citric acid (with 16 g/L sucrose added to control for residual sucrose in the *A. niger* supernatant). Cryopreserved culture of *Bacillus* sp. NRRL 14202O (obtained from USDA ARS culture collection) was isolation streaked onto NGPP agar media and incubated for 24 hours at 40° C. After 24 hours of incubation, mucoid colonies from the plates were used to inoculate three liquid cultures consisting of 25 mL NGPP media formulated with fungal supernatant in 125 mL sterile flasks, and three control cultures consisting of 25 mL NGPP media formulated with commercial citric acid in 125 mL sterile flasks. The cultures were incubated for 72 hours at 40° C. with gentle shaking (150-200 rpm), and 1 mL samples were aseptically removed every 24 hours to measure cell growth (optical density at 600 nm wavelength, $OD_{600}$) and analyze PGA production. PGA production was preliminarily assessed by increased viscosity of the cultures. PGA production was confirmed and quantified by centrifuging culture broth to remove cellular material, and analyzing the resulting supernatant with SDS-PAGE and methylene blue staining (described below in Analytical methods: "PGA quantification via SDS-PAGE").

Analytical Methods

PGA quantification via SDS-PAGE. PGA was quantified by SDS-PAGE followed by methylene blue staining. A calibration ladder of 0.25, 0.5, 0.75, 1.0, 1.25, and 1.5 µg PGA (commercially purchased from Sigma-Aldrich) was used to construct a standard curve in order to quantify PGA purified from co-culture fermentation broth via densitometry. Each culture sample was centrifuged and resulting cell-free supernatant diluted to fit into calibration range (often two to three dilutions were used to insure data fit into calibration range). 15 µL of diluted sample was mixed with 15 µL of 2× Laemmli Buffer (Bio-Rad) and heated at 95° C. for 5 min. to ensure denaturation. 12 µL of each denatured/prepared sample was loaded into a well of a Criterion 4-15% SDS-PAGE gel (Criterion 4-20% Tris-HCl, 1.0 mm, 26 well comb, 15 µL). Gel was run for 55 min. at 200 Volts. ImageJ densitometry analysis was used to construct a standard curve to relate pixel intensity to PGA concentration. Densitometry of each sample was performed and related to PGA concentration via standard curve.

HPLC analysis of small molecule metabolites. Glycerol and citric acid, along with glutamic acid derivitization products, were quantified using high performance liquid chromatography (HPLC). Culture samples were centrifuged and resulting cell-free supernatant was filtered through a 0.22 µm membrane. Samples were then analyzed on an Agilent 1100 HPLC equipped with a Rezex ROA ion-exchange column, using 5 µL injection volume, 60° C. column temperature, 0.005N $H_2SO_4$ mobile phase at 0.5 mL/min., and a refractive index detector (RID) for analyte quantification.

Results

PGA production with agar plates prepared with *A. niger* NRRL 599 supernatant. Colony morphology for *Bacillus* sp.

NRRL 14202O was similar between NGGP plates prepared with fungal citric acid supernatant (solid-phase compartmentalized sequential culture) and commercial citric acid (control). Both types of media yielded large colonies with a wrinkled structure. Large amounts of mucoid material were evident upon visual inspection, suggesting strong PGA production on both the controls and plates prepared with fungal citric acid supernatant (FIG. 4B). PGA production on NGPP plates prepared with fungal citric acid supernatant (solid-phase compartmentalized sequential culture) was confirmed by performing SDS-PAGE with PGA-selective methylene blue staining, using synthetic PGA as a control; SDS-PAGE revealed a stained band of similar molecular weight to the synthetic PGA control for the solid-phase compartmentalized sequential culture samples. These results demonstrate that, under solid-substrate growth conditions, PGA producing *Bacillus* sp. are capable of robust growth and PGA production on the supernatant of citric acid producing *A. niger* species.

Figure 5:
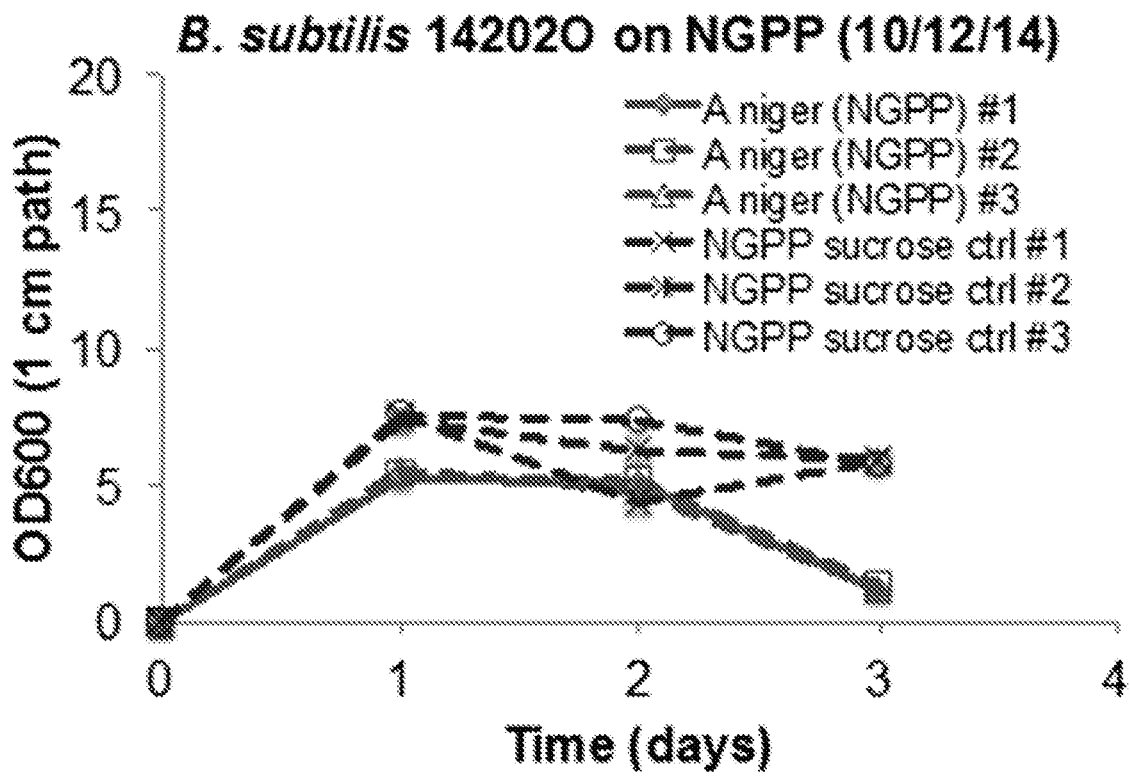
FIG. 5 shows PGA production with *Bacillus subtilis* NRRL 14202O (PGA titer, g/L, at endpoint) in compartmentalized sequential cultures ("*A. niger* (NGPP)" series) and control cultures formulated with commercial citric acid and with similar sucrose concentration to media formulated with *A. niger* supernatant ("NGPP sucrose ctrl" series).
Figure 6:
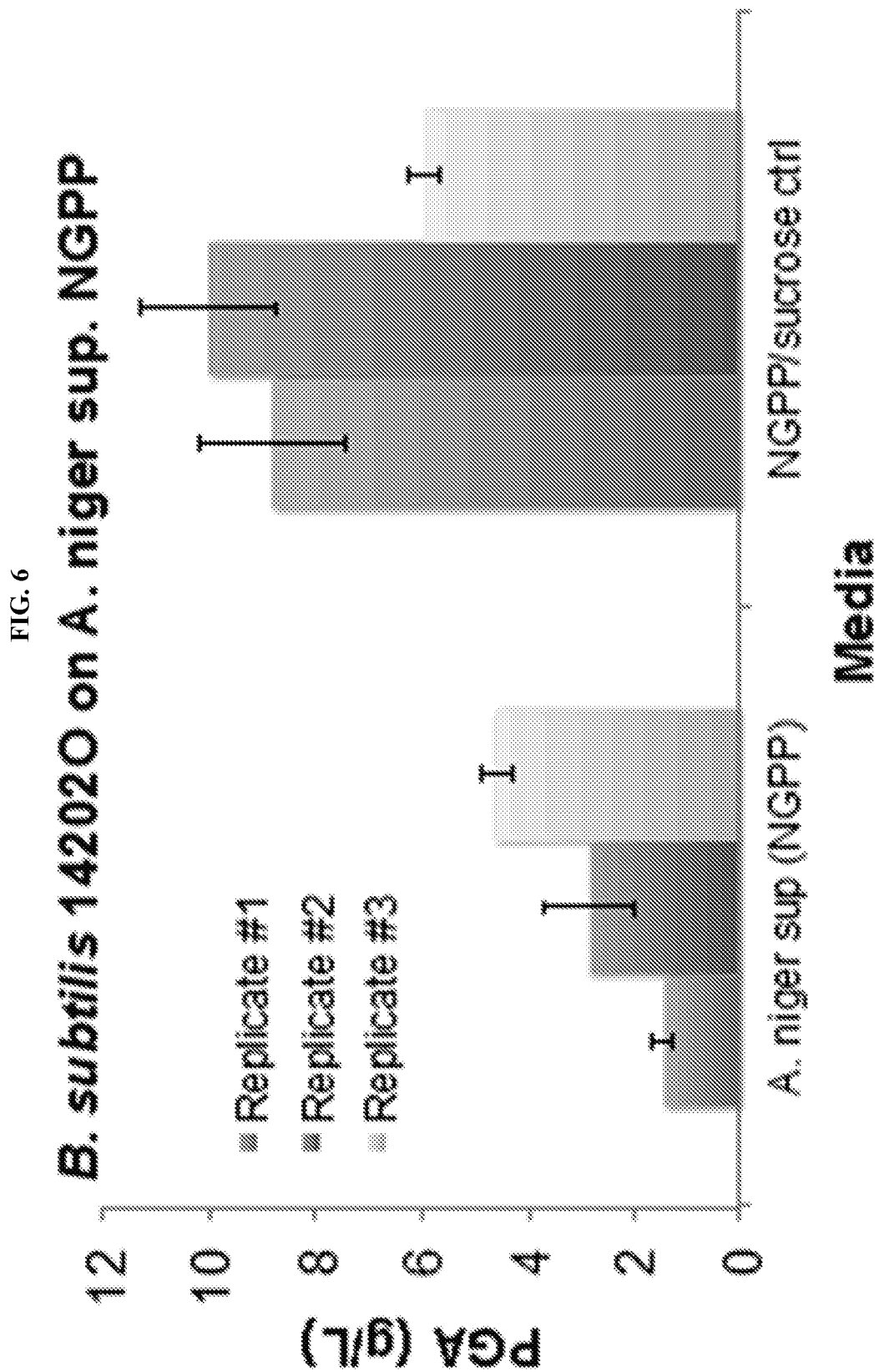

PGA production on liquid media prepared with *A. niger* NRRL 599 supernatant. Liquid cultures of *Bacillus* sp. NRRL 14202O in NGPP media prepared with fungal citric acid supernatant (compartmentalized sequential culture) and commercial citric acid (control) had similar growth profiles and reached similar cell densities (FIG. 5), although the compartmentalized sequential cultures had a slightly lower growth rate and maximum $OD_{600}$, and had a higher stationary phase death rate. Both the compartmentalized sequential cultures and controls produced PGA under liquid growth conditions (FIG. 6). Final PGA titer varied greatly between replicates in each sample set, however, the compartmentalized sequential cultures had a lower average titer compared to the controls (FIG. 6).

These results illustrate that PGA producing *Bacillus* sp. are capable of growth and PGA production on the supernatant of citric acid producing *A. niger* species under liquid culture conditions, but also show evidence that *A. niger* NRRL 599 may produce by-products that antagonize PGA production in *Bacillus* sp. NRRL 14202O, based on reduced PGA titer in compartmentalized sequential cultures compared to the controls.

Example 2

PGA Production via Compartmentalized Sequential Co-Cultures and Consolidated Sequential Co-Cultures of *Y. lipolytica* NRRL 1094 and Glutamate-independent PGA producing *Bacillus* sp. ER1064

This experiment was performed to demonstrate PGA production via compartmentalized sequential cultures and consolidated sequential cultures of *Y. lipolytica* and glutamate/glutamine-independent PGA producing *Bacillus* sp. In the citric acid accumulation phase, *Y. lipolytica* was cultured under permissive conditions to allow requisite amount of citric acid to be produced before initiation of PGA production phase (usually 72-96 hrs after *Y. lipolytica* inoculation). To begin PGA production phase, PGA producing *Bacillus* sp. was cultured under permissive conditions using *Y. lipolytica* supernatants. In compartmentalized sequential co-culture experiment (e.g., the method depicted in FIG. 2), all *Y. lipolytica* cells were removed via sterile filtration, while in the consolidated co-culture experiment, *Y. lipolytica* cells were not removed (e.g., the method depicted in FIG. 3). As a control, *Bacillus* sp. was cultured on an entirely synthetic "mock-up" medium, which simulates the composition of *Y. lipolytica* supernatant. In this way, *Bacillus* sp. was cultured with nutrient levels/pH identical to an actual *Y. lipolytica* supernatant, but without ever coming into contact with any secondary metabolites/extracellular components resulting from *Y. lipolytica* growth. Each experiment and control was performed in biological triplicates; two sets of triplicates were performed for the consolidated sequential co-culture experiment. The naming convention for the experimental samples is as follows:

Culture Labeling Scheme

A1-3: Compartmentalized Sequential Co-Culture (Corresponding to Method in FIG. 2)
B1-6: Consolidated Sequential Co-Culture (Corresponding to Method in FIG. 3)
C1-3: Control (*Y. lipolytica* Supernatant Mock-Up Media w/*Bacillus* sp.)

Materials and Methods

Figure 7:
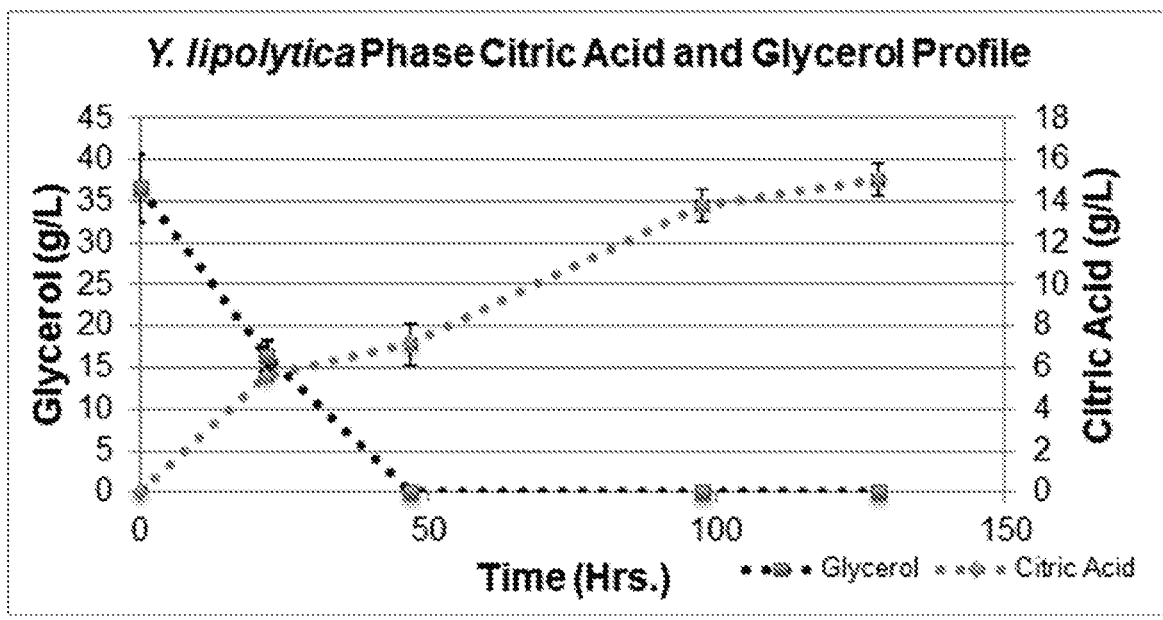
FIG. 7 shows citric acid production and glycerol consumption in *Y. lipolytica* cultures (prior to inoculation with *Bacillus* sp)
Figure 8:
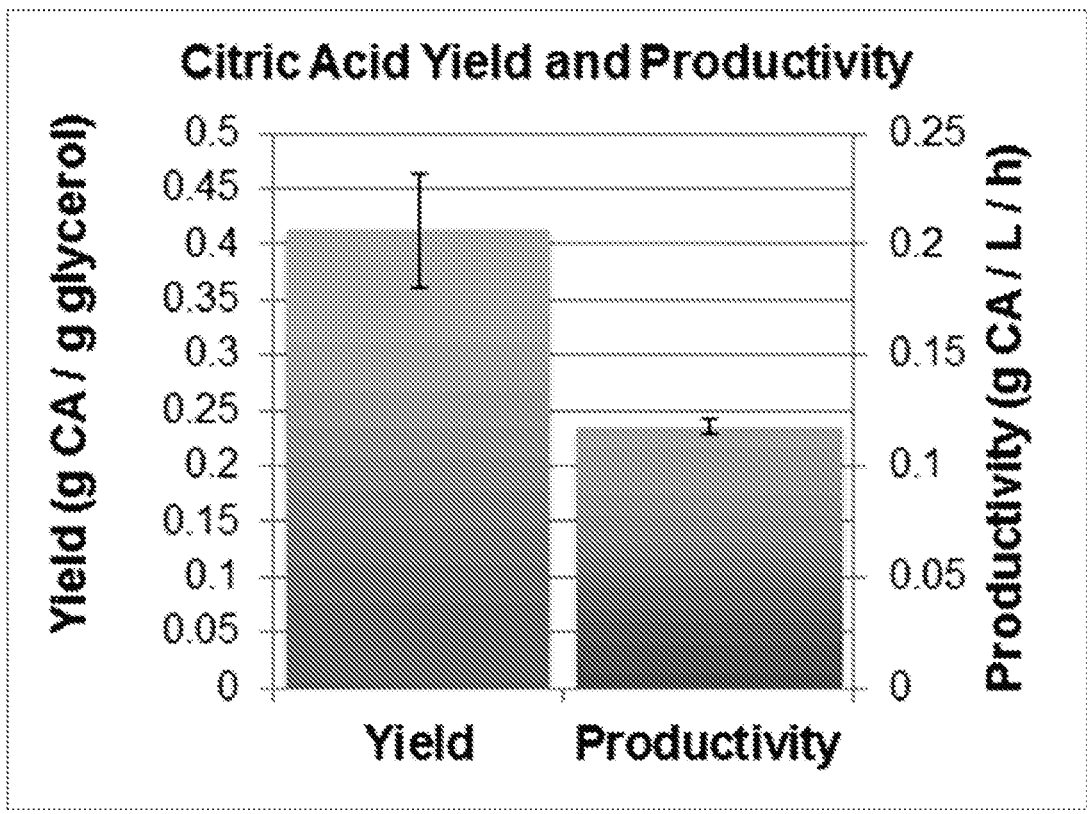
FIG. 8 shows citric acid yield in *Y. lipolytica* cultures (prior to inoculation with *Bacillus* sp)

Citric acid production with *Y. lipolytica* NRRL 1094. 30 mL sterile Tryptic Soy Digest (TSB) broth was inoculated with cryopreserved *Y. lipolytica* NRRL 1094 cells (obtained from USDA ARS culture collection). The inoculated culture was incubated for 24 hrs at 30° C. and 180 rpm. After 24 hours, 2 mL of culture was aseptically transferred to sterile 125 mL shaker flasks (9×total replicates) containing 20 mL of sterile citric acid production media consisting of: 1.7 g/L $KH_2PO_4$, 12 g/L $Na_2HPO_4$, 1.25 g/L $MgSO_4*7H_2O$; 0.25 g/L $(NH_2)_2SO_4$, 40 g/L Glycerol, 0.006 g/L Thiamine HCl, 0.25 g/L Yeast Extract, and at pH 6.0. Culture was incubated at 30° C. at 180 rpm. Periodically, 1 mL samples were removed aseptically to monitor citric acid production/glycerol consumption via HPLC (described in "Analytical Methods: HPLC analysis of small molecule metabolites"). Culture pH was maintained at 6 through addition of sterile 2 M NaOH to allow optimal citric acid production. After 128 hours of incubation, all glycerol (40 g/L) was consumed by the cultures, with 15+/−0.8 g/L citric acid produced (FIG. 7). The overall yield of citric acid was 0.4+/−0.05 g citric acid/g glycerol, with a citric acid productivity of 0.118+/−0.004 g/L/h (FIG. 8).

PGA production on liquid media prepared with *Y. lipolytica* NRRL 1094 cell-free supernatant (compartmentalized sequential co-cultures). Compartmentalized sequential co-cultures (A1-3, three replicates total), were carried out as follows. After the citric acid fermentation was completed, *Y. lipolytica* cells were removed from an aliquot of *Y. lipolytica* fermentation broth via aseptic filtration through a 0.22 µm membrane, and the pH of the supernatant was adjusted to 7. Non-glycolytic precursor PGA production media (NGPP) ingredients were added as concentrated solutions directly to the cell-free *Y. lipolytica* supernatant, which served as the citric acid source, the final composition consisted of: 1.7 g/L $KH_2PO_4$, 12 g/L $Na_2PO_4$, 1.25 g/L $MgSO_4*7H_2O$, 0.05 g/L $FeCl_3*6H_2O$, 0.2 g/L $CaCl_2*2H_2O$, 14.5 g/L $(NH_4)_2SO_4$, 0.0005 g/L biotin. 48 hours prior to completion of citric acid fermentation, cryopreserved culture of *Bacillus* sp. ER1064 (isolation index "NRRL_14202_Mod_1_3_15", NRRL 14202 mutant, obtained from Ecovia Renewables L.L.C.) was isolation streaked onto NGPP agar media and incubated for 24 hours at 40° C. After 24 hours of incubation, mucoid colonies from the plate were used to inoculate 30 mL inoculum media (NGPP "mod. 1" media), consisting of 1.0 g/L $KH_2PO_4$, 1.0 g/L K$_2$HPO4, 1.25 g/L $MgSO_4*7H_2O$, 0.05 g/L $FeCl_3*6H_2O$, 0.2 g/L $CaCl_2*2H_2O$, 14.5 g/L $(NH_4)_2SO_4$, 0.0005 g/L biotin, pH 7. Inoculum was incubated at 40° C.

at 180 rpm for 24 hours. After 24 hours, 2 mL of inoculum was aseptically transferred to sterile 125 mL shaker flasks containing 20 mL of prepared NGPP "mod. 1"/*Y. lipolytica* supernatant media and allowed to incubate at 40° C. at 180 rpm for 67 hours. Experiments were performed in biological triplicates. 1 mL culture samples were aseptically removed periodically to monitor glycerol and citric acid consumption via HPLC (described below in "Analytical Methods: HPLC analysis of small molecule metabolites"), measure cell growth (optical density at 600 nm wavelength, $OD_{600}$), and analyze PGA production (described in "Analytical methods: PGA quantification via SDS-PAGE")

PGA production on liquid media prepared with *Y. lipolytica* NRRL 1094 fermentation broth (consolidated sequential co-cultures). Consolidated sequential co-cultures, (B1-6, six replicates total), were carried out in exactly the same manner as cultures A1-3 described in "PGA production on liquid media prepared with *Y. lipolytica* NRRL 1094 cell-free supernatant." However, the *Y. lipolytica* cells were not removed.

Controls. A control set of triplicates (C1-3) was implemented using a synthetic "mock-up" medium (utilizing commercially purchased citric acid). The media formulation consisted of the same nutrient and pH level as "NGPP mod. 1/*Y. lipolytica* supernatant" (described above). Cultures were performed, samples, and analyzed in exactly the same manner as those described above.

Results

Figure 9:
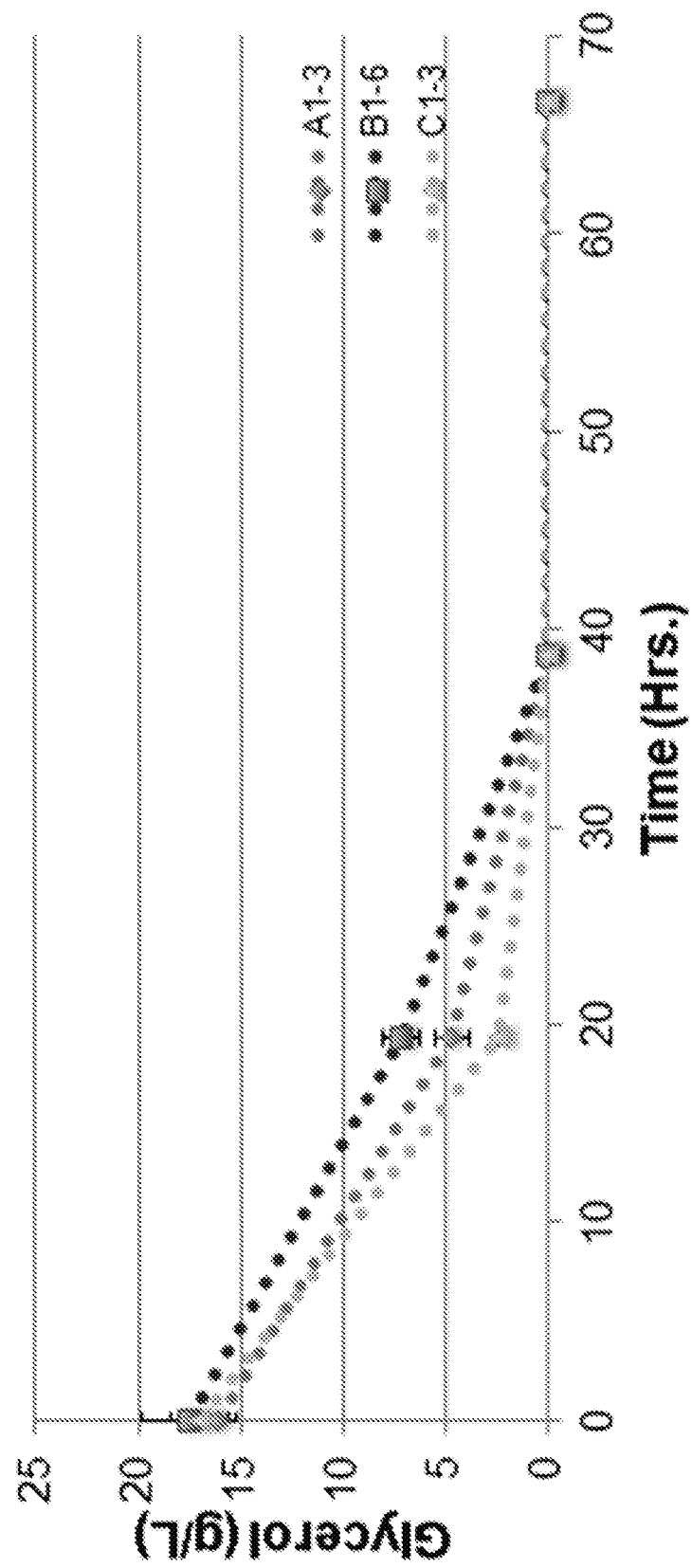
FIG. 9 shows glycerol consumption in compartmentalized sequential co-cultures (A1-3), consolidated sequential co-cultures (B1-6), and controls (C1-3)
Figure 10:
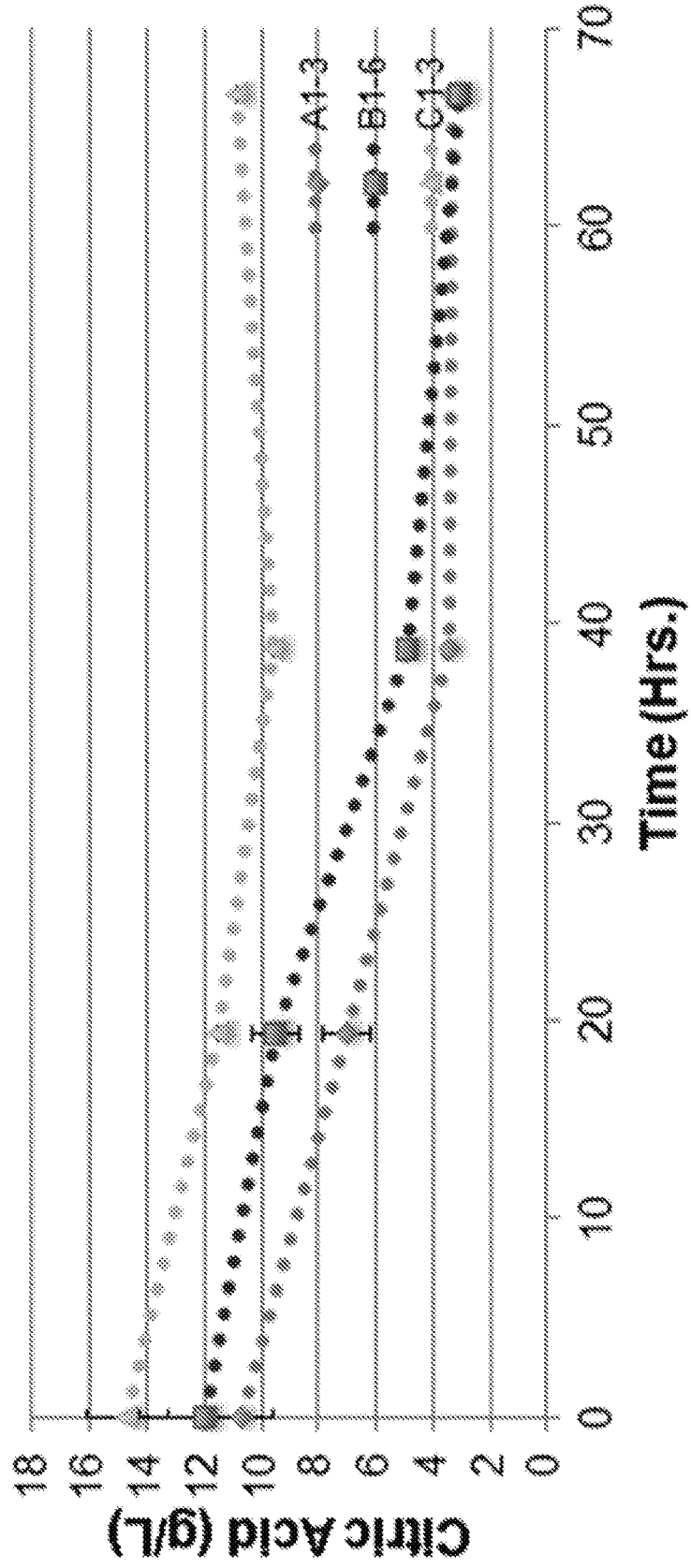
FIG. 10 shows citric acid consumption in compartmentalized sequential co-cultures (A1-3), consolidated sequential co-cultures (B1-6), and controls (C1-3)
Figure 11:
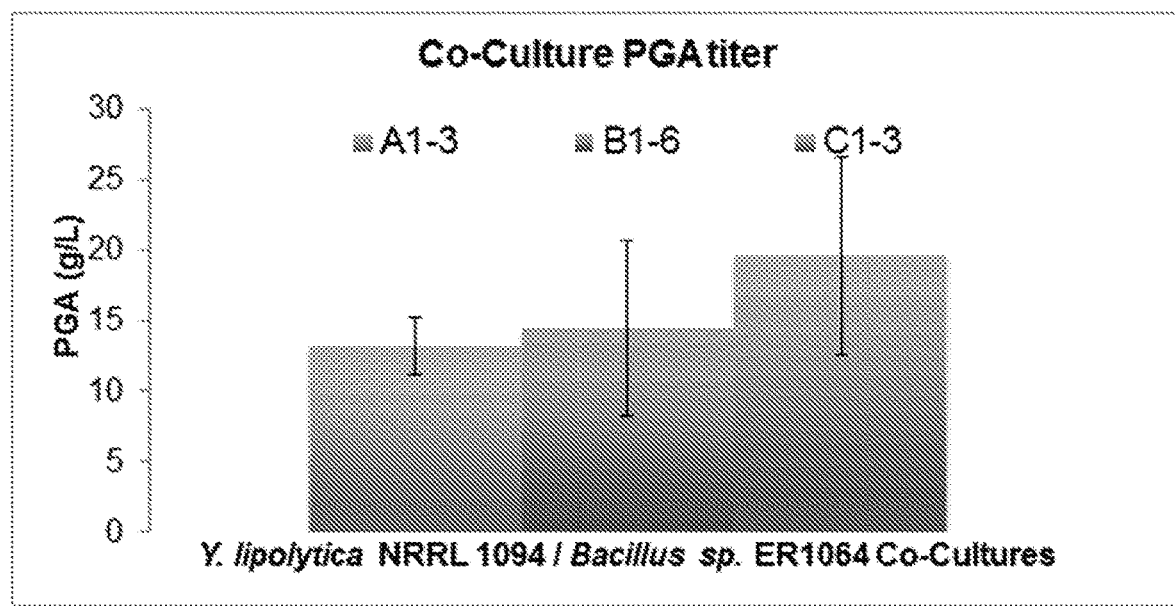
FIG. 11 shows PGA titer for *Y. lipolytica* NRRL 1094/ *Bacillus* sp. ER1064 compartmentalized sequential co-cultures (A1-3), consolidated sequential co-cultures (B1-6), and controls (C1-3)
Figure 12:
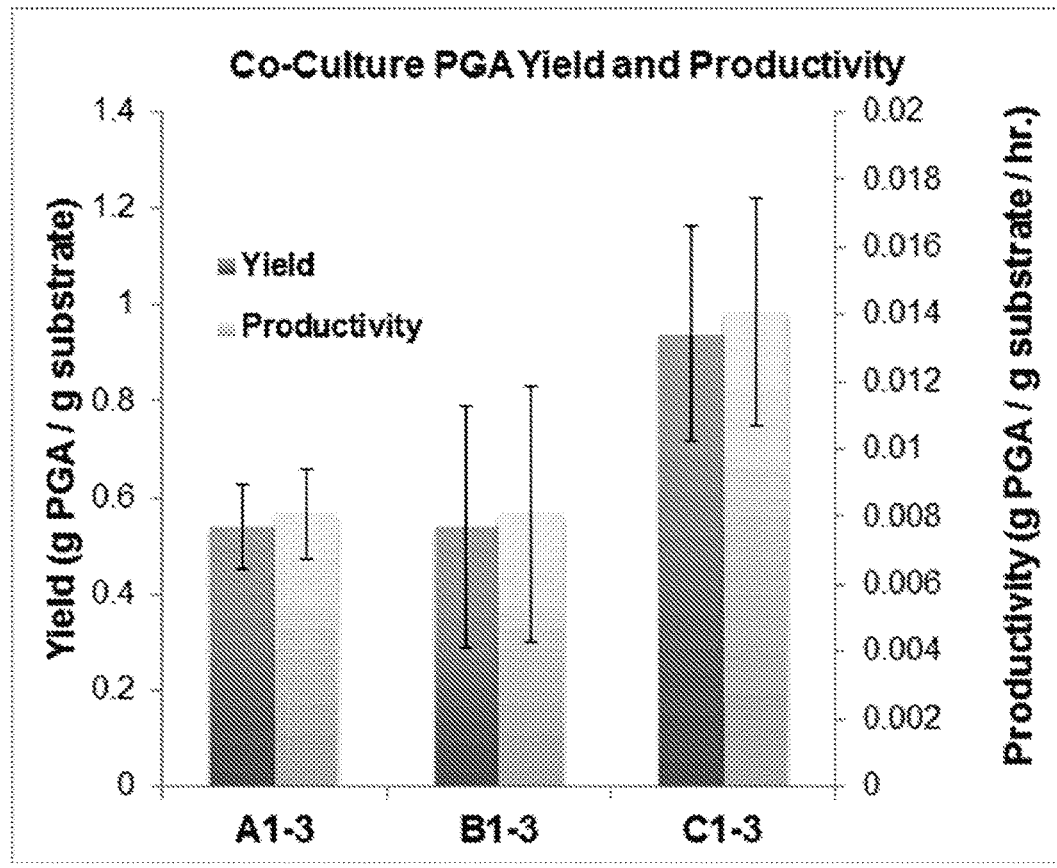
FIG. 12 shows PGA yield and productivity for *Y. lipolytica* NRRL 1094/*Bacillus* sp. ER1064 compartmentalized sequential co-cultures (A1-3), consolidated sequential co-cultures (B1-6), and controls (C1-3)

PGA production on liquid media prepared with *Y. lipolytica* NRRL 1094 cell-free supernatant (compartmentalized sequential co-cultures). Liquid cultures of glutamic acid/glutamine independent PGA producing *Bacillus* sp. ER1064 in NGPP "mod. 1" prepared with *Y. lipolytica* citric acid supernatant (compartmentalized sequential co-culture, A1-3) and commercial citric acid (control, C1-3) produced 12.7+/−2.0 g/L PGA and 19.6+/−7.0 g/L PGA, with an overall yield of 0.5+/−0.1 g/g and 0.9+/−0.4 g/g, respectively (FIGS. 11 & 12). The compartmentalized sequential co-cultures (A1-3) consumed all available glycerol (16.1+/−0.03 g/L) and most of available citric acid (FIGS. 9 & 10), while the controls (C1-3) consumed similarly all glycerol but less citric acid (FIGS. 9 & 10).

PGA production on liquid media prepared with *Y. lipolytica* NRRL 1094 fermentation broth (consolidated sequential co-cultures). *Y. lipolytica* NRRL 1094/*Bacillus* sp. ER1064 consolidated sequential co-cultures (B1-6) in NGPP "mod. 1" media produced 14.4+/−6.2 g/L with overall yield of 0.54+/−0.24 g/g (FIGS. 11 & 12). Co-cultures B1-6 consumed all available glycerol and the majority of available citric acid (FIGS. 9 & 10); glycerol and citric acid consumption profiles were qualitatively similar between the compartmentalized sequential co-cultures (A1-3) and consolidated sequential co-cultures (B1-6).

Overall, these results indicate that glutamic acid/glutamine independent PGA producing *Bacillus* sp. are capable of growth and PGA production on the supernatant of citric acid producing *Y. lipolytica* NRRL 1094 without induction via exogenous glutamic acid or glutamine. There is not a statistically significant difference in PGA titer, yield, and productivity between the compartmentalized sequential co-cultures (A1-3), consolidated sequential co-cultures (B1-6) and controls (C1-3). However, PGA production performance of control cultures (C1-3) is better, possibly indicating potential inhibitory effects upon PGA production due to extracellular components produced during citric acid fermentation. The consolidated sequential co-cultures (B1-6) performed very comparably to the compartmentalized sequential co-cultures (A1-3). This result indicates that *Y. lipolytica* cells (present in consolidated sequential co-cultures) do not compete with *Bacillus* sp. for nutrients or release antibacterial compounds.

Example 3

Optimization of Culture Methods
Selection of *Bacillus* sp. Strains for Co-Cultures For optimal and cost-effective PGA production under co-culture conditions, *Bacillus* sp. strains with high PGA production (as quantified by titer, yield, and productivity), minimal nutrition requirements, and tolerance to feedstock inhibitors and fungal fermentation by-products are advantageous. Based on these criteria, three prototrophic *Bacillus* sp. isolates (designated as strains ER1001, ER1007, and ER1012; obtained from Ecovia Renewables Inc.), with high PGA production and ability to grow on biodiesel waste glycerol, were selected for evaluation in co-culture.

Figure 13:
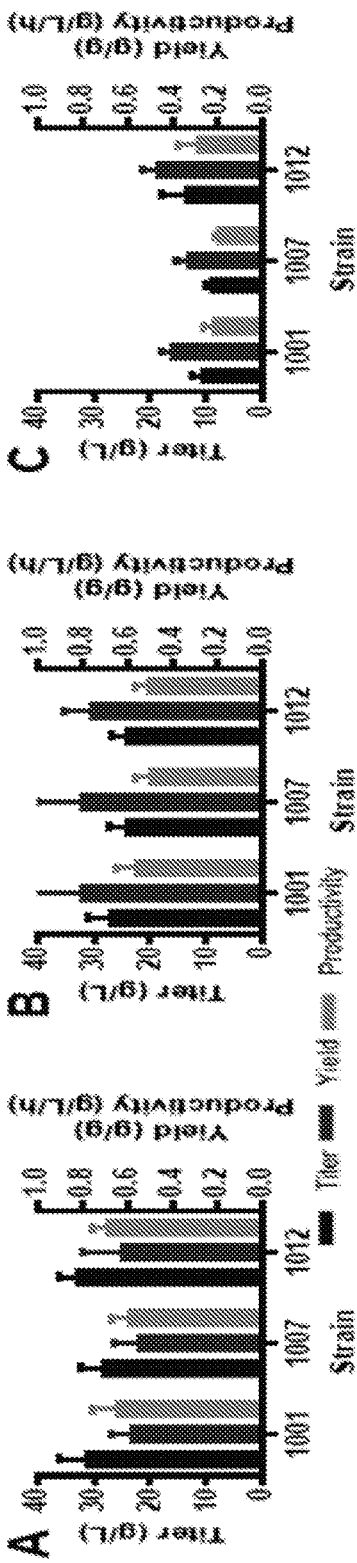
FIG. 13 shows PGA titer (g/L), yield (g/g C sources), and productivity (g/L/h) for mono-cultures of *Bacillus* sp. strains ER1001, ER1007, and ER1012 on: (A) rich screening media (C sources: 0.7 g/L yeast extract, 3.5 g/L peptone, 31.5 g/L glutamic acid, 14 g/L citric acid, and 14 g/L glycerol), (B) minimal media (C sources: 22.7 g/L citric acid, and 14 g/L glycerol), and (C) minimal media formulated with biodiesel waste glycerol (C sources: 14 g/L citric acid, and 14 g/L glycerol).

For reference and comparative purposes, the mono-culture performance and characteristics of these strains are briefly described (FIG. 13). Under mono-culture conditions, ER1001, ER1007, and ER1012 produce high MW (~1000 kDa) PGA with high titer (28±4 to 32±3 g/L), yield (0.56±0.1 to 0.63±0.2 g/g; 71±10 to 80±20% theoretical), and productivity (0.60±0.08 to 0.69±0.06 g/L/h) in rich media (FIG. 13A). Furthermore, in "mock-up" minimal media, approximately simulating co-culture conditions (containing only salts, inorganic N source, and glycerol/citric acid as C sources), mono-cultures of these strains are capable of growth and PGA production (FIG. 13B). The slightly lower titers in minimal media (FIG. 13B vs. 13A) are likely due to lower C source concentration (thus limiting available substrates for PGA production), which is reduced to 36.7 g/L total C sources in the minimal media formulation compared to 63.7 g/L total C sources in the rich media formulation due to elimination of yeast extract, peptone, and glutamic acid from the minimal media. Furthermore, mono-cultures of *Bacillus* sp. strains ER1001, ER1007, and ER1012 are capable of growth and PGA production on waste glycerol media (FIG. 13C), but performance is reduced compared to model rich and minimal media, likely due to inhibitors present in waste glycerol (high salt concentration, free fatty acids, etc). While performance between isolates was comparable in model media, on waste glycerol ER1012 appeared to slightly outperform the others (FIG. 13C).

Optimization of Different Co-Culture Schemes

Figure 14:
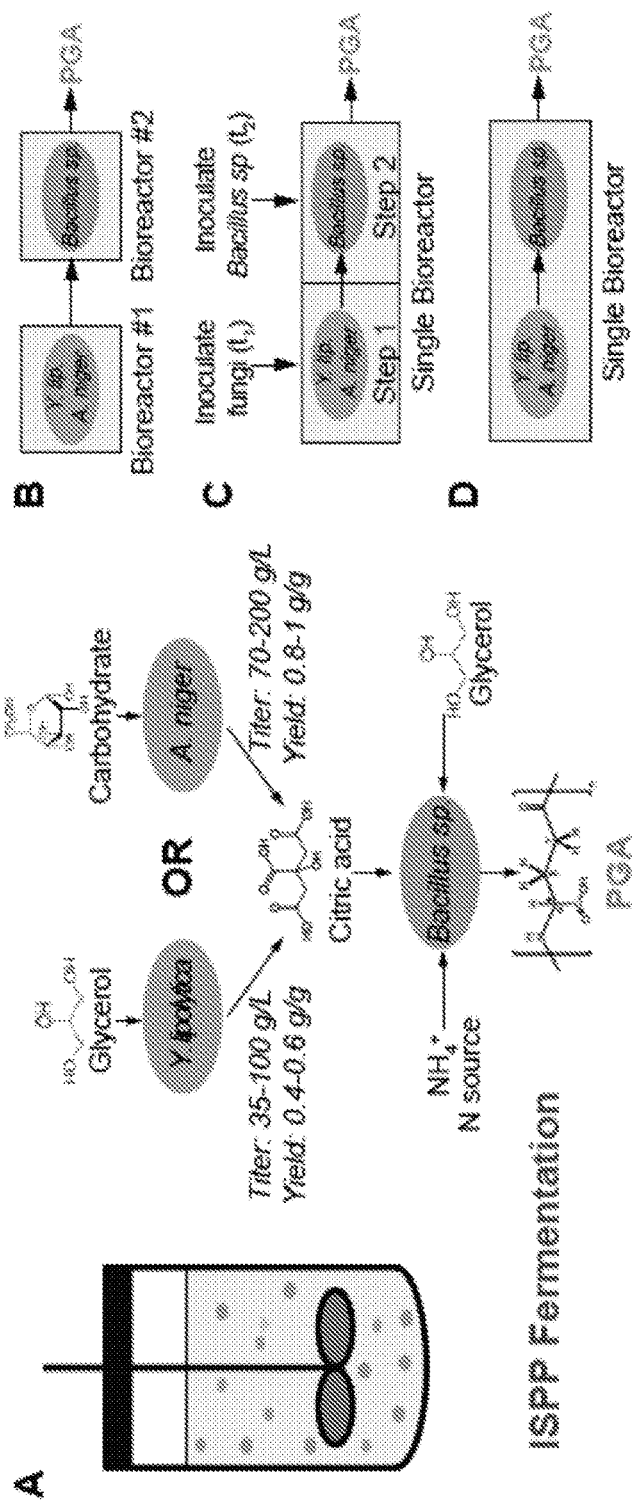
FIG. 14 shows (A) Production of PGA/via in-situ precursor production (ISPP). (B) Compartmentalized sequential culture scheme (C) Consolidated sequential culture scheme (D) Simultaneous co-culture scheme.

Three different bioprocessing schemes for ISPP co-cultures were considered:
i) Compartmentalized sequential cultures (FIG. 14B): In this scheme, citric acid producing fungi are cultured in a bioreactor under permissive conditions. Culture broth is then transferred to a second bioreactor, charged with additional nutrients/glycerol, and then fermented with PGA producing *Bacillus* sp.
ii) Consolidated sequential cultures (FIG. 14C): In this scheme, citric acid producing fungi are cultured in a bioreactor under permissive conditions. After the citric acid fermentation is finished, the bioreactor is charged with additional nutrients/glycerol, and inoculated with a PGA producing *Bacillus* sp.

iii) Simultaneous co-cultures (FIG. 14A&D): In this scheme, citric acid producing fungi are co-cultured with PGA producing *Bacillus* sp. to achieve concurrent citric acid and PGA production.

Implementation of simultaneous co-cultures presented challenges due to physiological and ecological incompatibility between PGA producing *Bacillus* sp. and citric acid producing fungi. PGA production by *Bacillus* sp. is generally favored by low carbon:nitrogen (C:N) and carbon:phosphorus (C:P) ratios, high temperature (37° C. to 45° C.), moderate pH (6.5 to 7.5), and presence of trace metal ions, especially $Mn^{2+}$ (Bajaj, I. and R. Singhal, Poly (glutamic acid)—an emerging biopolymer of commercial interest. Bioresour Technol, 2011. 102(10): p. 5551-61). Fungi such as *A. niger* and *Y. lipolytica* produce citric acid as a result of spillover metabolism caused by physiological imbalances (Roehr, M., C. P. Kubicek, and J. Kominek, Citric Acid, in Biotechnology Set. 2008, Wiley-VCH Verlag GmbH. p. 307-345). Thus, in contrast to PGA, conditions favoring citric acid production include high C:N and C:P ratios, moderate growth temperatures (25° C.-30° C.), low concentration of trace metals (especially $Mn^{2+}$), and for *A. niger*, low pH (2 to 3) (Roehr et al., supra). In addition to these environmental incompatibilities, initial studies identified significant antagonistic interactions between *Bacillus* sp. and citric acid producing fungi; for example, in simultaneous co-cultures of *Bacillus* sp. ER1001 and *Y. lipolytica* NRRL 1094, *Y. lipolytica* was observed to decline from an initial cell density of ~$10^6$ cells/mL to <$10^2$ cells/mL within 24 hours.

Numerous strategies were considered to address strain compatibility issues, such as engineering citric acid producing fungi to modulate nitrogen uptake, or knocking out pathways for antifungal metabolites in *Bacillus* sp.

Compartmentalized sequential cultures were implemented and characterized with *Bacillus* sp. isolates ER1001, ER1007, and ER1012, with either *Y. lipolytica* NRRL 1094 or *A. niger* NRRL 599 for the citric acid production step. These citric acid producing fungi were previously identified as promising candidates for ISPP co-cultures. *Y. lipolytica* is a yeast capable of metabolizing glycerol to citric acid, and thus enables an ISPP fermentation that utilizes low-cost waste glycerol as the sole C source (Rymowicz, W., et al., 2006. 60(5): p. 391-394). In contrast, *A. niger* is a filamentous fungus that ferments carbohydrates (a more expensive feedstock) to citric acid, but achieves up to twice the citric acid titer/yield of *Y. lipolytica* and is used for commercial citric acid production (Roehr et al., supra).

Each of the selected *Bacillus* sp. isolates (ER1001, ER1007, and ER1012) was evaluated in sequential culture studies with *Y. lipolytica* NRRL 1094 (glycerol as substrate for citric acid) and in studies with *A. niger* NRRL 599 (sucrose or glucose as substrate for citric acid), using species appropriate minimal media for the fungal fermentation step, and *Bacillus* sp. minimal media (14 g/L glycerol and 13.7 to 22.7 g/L citric acid from fungal fermentation) for the PGA production phase. For the citric acid production step in these studies, *Y. lipolytica* NRRL 1094 typically achieved 35 to 40 g/L citric acid titer, with yield of 0.4 to 0.45 g/g-glycerol, while *A. niger* NRRL 599 reached titers of 75 to 100 g/L, with yields up to 0.85 g/g-sugar. Studies with *Bacillus* sp. isolates/*Y. lipolytica* NRRL 1094 were also completed using biodiesel waste glycerol, for both citric acid and PGA production phases. *Bacillus* sp. monocultures were performed in parallel, which served as controls/references for each study.

Figure 15:
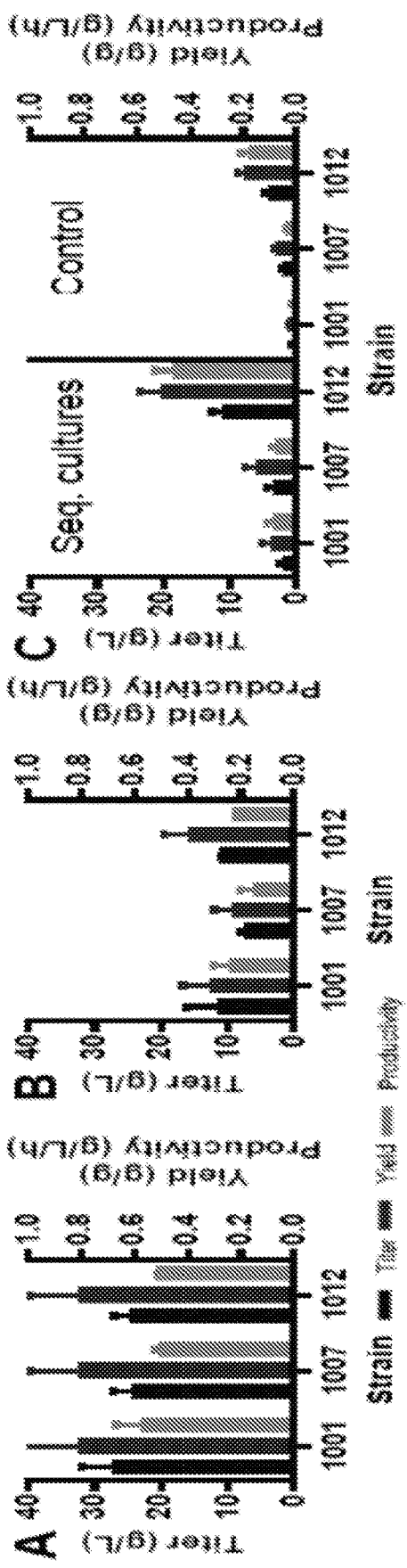
FIG. 15 shows PGA titer (g/L), yield (g/g C sources), and productivity (g/L/h) in sequential cultures. (A) PGA production with *Bacillus* sp./*Y. lipolytica* NRRL 1094 on minimal media. (B) PGA production with *Bacillus* sp./*Y. lipolytica* on minimal waste glycerol media. (C) PGA production with *Bacillus* sp./*A. niger* 599 on minimal media, with *Bacillus* sp. monoculture controls.

All three of the *Bacillus* sp. isolates tested were capable of growth and PGA production in compartmentalized sequential cultures with *Y. lipolytica* NRRL 1094 or *A. niger* NRRL 599 (FIG. 15). For sequential cultures with *Y. lipolytica* NRRL 1094, PGA titers ranged from 24±3 to 27±5 g/L (productivity of 0.5±0.02 to 0.6±0.1 g/L/h), with yields around 0.8±0.2 g/g (120±30% theoretical) in model media (FIG. 15A). In waste glycerol media, PGA titer, yield, and productivity were reduced by approximately one half compared to model media (FIG. 15B). PGA production was lower in *A. niger* NRRL 599 sequential cultures compared to *Y. lipolytica* NRRL 1094 (FIG. 15C). However, PGA production was also reduced in the monoculture controls run concurrently with the *A. niger* NRRL 599 study (FIG. 15C). While *Y. lipolytica*/*Bacillus* sp. sequential cultures outperform those with *A. niger* in preliminary tests (FIG. 15A vs. 15C), sequential cultures with *A. niger* may be more advantageous for commercialization, due to higher citric acid titer/yield and use of *A. niger* in commercial citric acid production.

Overall, PGA production was comparable between sequential cultures with *Y. lipolytica* NRRL 1094 and *Bacillus* sp monocultures (FIG. 13B vs. FIG. 15A). However, in waste glycerol media and with *A. niger* NRRL 599 sequential cultures, PGA production was reduced relative to monocultures. Since microbial metabolism can be highly dependent upon environmental/physiological context, strain behavior may differ between monoculture and co-culture conditions, as has been observed in previous work (Minty, J. J., et al., Proc Natl Acad Sci USA, 2013. 110(36): p. 14592-7). In particular, *Y. lipolytica* and *A. niger* are both known to produce numerous secondary metabolites (Bourdichon, F., et al., International journal of food microbiology, 2012. 154(3): p. 87-97) that could be antibacterial or otherwise affect *Bacillus* sp. physiology. *Bacillus* sp. isolate ER1012 had superior PGA titer/yield on waste glycerol media and in sequential culture with *A. niger* NRRL 599 (FIG. 15C), indicating that this isolate may have higher intrinsic stress tolerance compared to the others.

Bioreactor Co-Cultures & Demonstration of Co-Culture Process Integration

An assessment of scale-up/process-integration technical risks was performed by conducting benchtop bioreactor-scale scale monocultures and ISPP sequential cultures, and through experimental evaluation of PGA separation methods.

Initial bioreactor studies focused on first scaling-up *Bacillus* sp. monoculture fermentations. Initial *Bacillus* sp. monoculture fermentations were conducted on rich media with *Bacillus* sp. isolate ER1001 at 2.5 L culture scale, using a New Brunswick Scientific Bioflo 3000 Bioreactor. After successfully implementing bioreactor scale ER1001 monocultures, ISPP sequential cultures with *A. niger* NRRL 599/*Bacillus* sp. ER1001 on minimal media (using sucrose as carbon source for *A. niger*) were implemented at 2.5 L scale.

Figure 16:
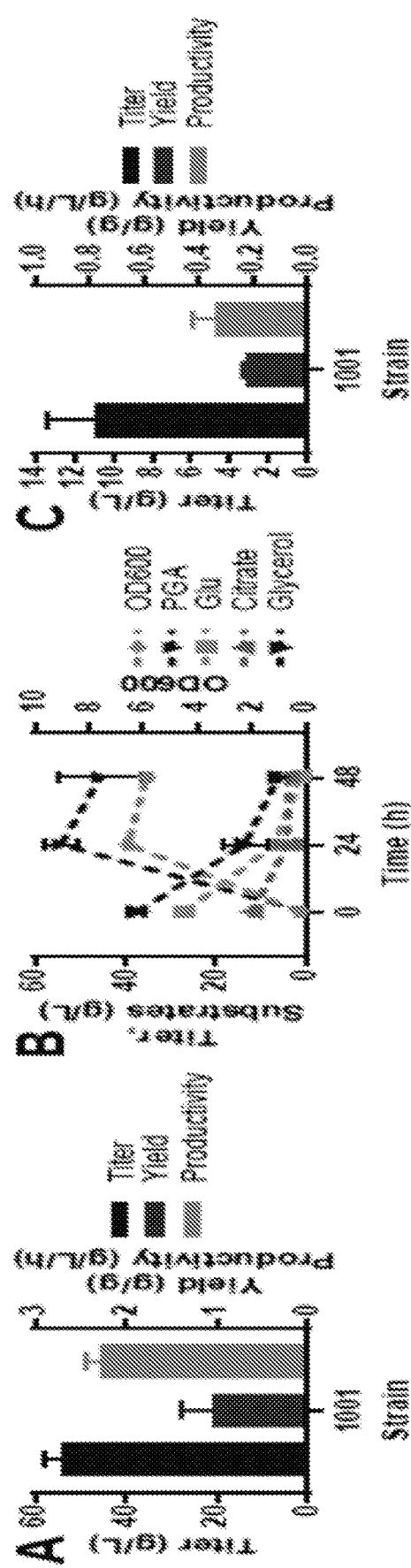
FIG. 16 shows fermentation performance at 2.5 L bioreactor scale. (A) PGA titer (g/L), yield (g/g), and productivity (g/L/h) for *Bacillus* sp. ER1001 monoculture in rich media. (B) Cell density (OD600), PGA titer (g/L), and substrate concentrations (g/L) for *Bacillus* sp. ER1001 monoculture in rich media. (C) PGA titer (g/L), yield (g/g), and productivity (g/L/h) for sequential culture of *Bacillus* sp. ER1001/*A. niger* NRRL 599 in minimal media.

Severe foaming occurred in initial studies (resulting in culture loss and poor PGA production), likely due to the secretion of surface-active molecules by *Bacillus* sp. ER1001 and culture broth viscosity. Commercially available antifoams were tested, but found to be ineffective. Through a short optimization study, a foam control protocol was developed that entailed augmenting media with antifoam 204 and 2.5% w/v NaCl, and reducing aeration to 0.1 to 0.2 vvm for the first 18 to 24 hours of fermentation. After achieving foam control, fermentation performance of 2.5 L scale ER1001 bioreactor cultures significantly exceeded flask-scale cultures, with 54±4 g/L PGA titer, 1±0.3 g/g C sources yield (130±47% theoretical), and 2.3±0.5 g/L/h productivity (FIG. 16A&B). Likewise, 2.5 L bioreactor-scale ISPP sequential cultures of *A. niger* NRRL 599/ *Bacillus* sp. ER1001 in minimal media also substantially outperformed flask-scale cultures, with 11±2.6 g/L PGA titer (0.34±0.08 g/L/h productivity), and 0.22±0.02 g/g C sources yield (29±3% theoretical) (FIG. 16C).

High purity PGA is required for numerous applications, such as personal care; for example, manufacturers have stringent specifications for color, odor, microbial contamination (CFU/g), and organic extractables. Key purification aspects/considerations include separating microbial cells from culture broth, removal of bulk salts and organic contaminants (residual fermentation substrates, etc.), and removal of problematic trace contaminants (including color/ odor compounds) The best method identified for cell removal was centrifugation of acidified fermentation broth (low pH minimizes zeta potential of cells and reduces PGA viscosity via pH dependent helix-coil transition (Do, J. H., H. N. Chang, and S. Y. Lee, 2001. 76(3): p. 219-223), which was employed in all studies. Subsequent purification of cell-free PGA broth was experimentally investigated using methods from literature for PGA/biopolymer purification (ethanol precipitation, $Cu^{2+}$ precipitation followed by dialysis, and tangential flow filtration (Bajaj, I. and R. Singhal-2011. 102(10): p. 5551-61)). For each purification method evaluated, PGA yield and % purity were measured.

Figure 17:
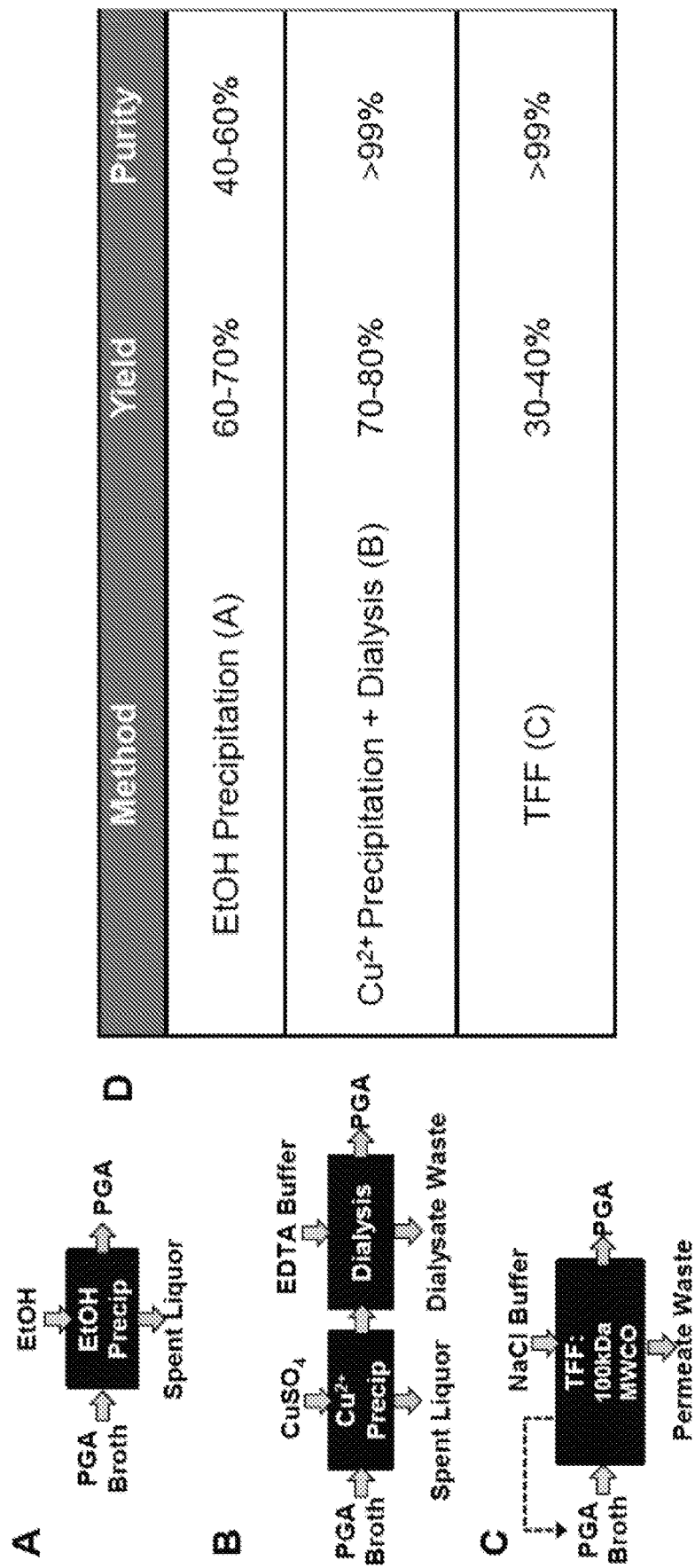
FIG. 17 shows a summary of purification studies: (A) Ethanol precipitation, (B) $Cu^{2+}$ precipitation, followed by dialysis, and (C) Tangential flow filtration (TFF). (D) Summary of results/insights for each method, with measured yield/purity ranges.

Results of each purification scheme are summarized in FIG. 17D. Out of the purification methods studied, PGA precipitation via ethanol or $Cu^{2+}$ gave the highest yields (FIG. 17A&B). Tangential flow filtration (TFF; FIG. 17C) gave excellent PGA purity, but despite the high MW of PGA, there was large yield loss to permeate (possibly due to compact structure of PGA at low pH). These results demonstrate that PGA produced via co-culture fermentation can be readily purified using the above described methods, yielding a commercially acceptable product.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

The invention claimed is:

1. A method of producing γ-polyglutamic acid (PGA), comprising:
   a) contacting an *Aspergillus niger, Yarrowia lipolytica,* or *Candida oleophila* fungus with a first feedstock in a bioreactor;
   b) fermenting said fungus to produce a culture broth comprising citric acid in the presence of a nitrogen source at a concentration of 0.1-50 g total N/L and a phosphorous source at a concentration of 0.1-25 g total P/L;
   c) contacting said bioreactor comprising said culture broth comprising citric acid from step b), without purification, with a *Bacillus* sp., wherein said *Bacillus* sp. is *Bacillus subtilis* or *Bacillus licheniformis* and a second feedstock; and
   d) fermenting said *Bacillus* sp. to generate PGA in the presence of a nitrogen source at a concentration of 0.1-50 g total N/L and a phosphorous source at a concentration of 0.1-25 g total P/L.

2. The method of claim 1, wherein one or more of steps a-d) further comprises the addition of one or more of glycerol, glutamate, or glutamine.

3. The method of claim 1, wherein said first and second feedstocks are selected from the group consisting of molasses, raffinate, pomace, fruit peels, corn starch, wheat starch, sorghum, brewery wastes, corn stover, spent algae cake, and glycerol.

4. The method of claim 3, wherein said first and second feedstocks are by-products from crop and food processing, biofuel or biochemical production, or biodiesel production.

5. The method of claim 3, wherein said first and second feedstocks are present at a concentration of 2.5-95% v/v or 50-250 g/L.

6. The method of claim 1, wherein said bioreactor comprises one or more components selected from the group consisting of a sparger, a mixing/agitation system, a temperature control system, a pH control system, and an antifoam control system.

7. The method of claim 6, wherein said mixing/agitation system is selected from the group consisting of impellers, turbines, and paddles driven by a motor.

8. The method of claim 1, wherein said step a) and/or b) further comprises contacting said fungus or bacteria with one or more additional components selected from the group consisting of a carbon source, a salt, and one or more additional nutrients.

9. The method of claim 8, wherein said nitrogen source is selected from the group consisting of yeast extract, peptone, tryptone, urea, corn steep liquor, malt extract, soy bean meal, soytone, $(NH_4)_2SO_4$, $NH_4Cl$, $NH_4NO_3$, $KNO_3$, and $NaNO_3$.

10. The method of claim 8, wherein said phosphorus source is selected from the group consisting of $KH_2PO_4$, $K_2HPO_4$, and $Na_2HPO_4$.

11. The method of claim 8, wherein said salts are selected from the group consisting of $KH_2PO_4$, $K_2HPO_4$, $Na_2HPO_4$, $MgSO_4$, $FeCl_3$, $FeCl_2$, $CaCl_2$, $MnSO_4$, $NaCl$, $KCl$, and $Na_2SO_4$.

12. The method of claim 8, wherein said one or more nutrients are biotin and/or vitamins.

* * * * *